United States Patent
Wang et al.

(10) Patent No.: US 12,403,142 B2
(45) Date of Patent: *Sep. 2, 2025

(54) COMBINATION THERAPY WITH A PHOSPHOINOSITIDE 3-KINASE INHIBITOR WITH A ZINC BINDING MOIETY

(71) Applicant: Curis, Inc., Lexington, MA (US)

(72) Inventors: Jing Wang, Lexington, MA (US); Troy David Patterson, Wilmington, MA (US); Ze Tian, Brookline, MA (US)

(73) Assignee: Curis, Inc., Lexington, MA (US)

( * ) Notice: Subject to any disclaimer, the term of this patent is extended or adjusted under 35 U.S.C. 154(b) by 879 days.

This patent is subject to a terminal disclaimer.

(21) Appl. No.: 17/557,567

(22) Filed: Dec. 21, 2021

(65) Prior Publication Data

US 2022/0249502 A1 Aug. 11, 2022

Related U.S. Application Data

(63) Continuation of application No. 16/565,921, filed on Sep. 10, 2019, now Pat. No. 11,234,986.

(60) Provisional application No. 62/729,648, filed on Sep. 11, 2018.

(51) Int. Cl.
| | |
|---|---|
| *A61K 31/5377* | (2006.01) |
| *A61K 9/20* | (2006.01) |
| *A61K 9/48* | (2006.01) |
| *C07K 16/28* | (2006.01) |

(52) U.S. Cl.
CPC ............ *A61K 31/5377* (2013.01); *A61K 9/20* (2013.01); *A61K 9/48* (2013.01); *C07K 16/2818* (2013.01)

(58) Field of Classification Search
CPC ........ A61K 31/5377; A61K 9/20; A61K 9/48; A61K 39/3955; A61K 45/06; C07K 16/2818; A61P 35/04
See application file for complete search history.

(56) References Cited

U.S. PATENT DOCUMENTS

| | | |
|---|---|---|
| 4,522,811 A | 6/1985 | Eppstein et al. |
| 5,484,596 A | 1/1996 | Hanna, Jr. et al. |
| 5,502,187 A | 3/1996 | Ayer et al. |
| 5,508,269 A | 4/1996 | Smith et al. |
| 5,767,068 A | 6/1998 | Vandevanter et al. |
| 6,014,969 A | 1/2000 | Lloyd et al. |
| 6,087,367 A | 7/2000 | Breslow et al. |
| 6,608,053 B2 | 8/2003 | Hayakawa et al. |
| 6,777,217 B1 | 8/2004 | Schreiber et al. |
| 7,300,935 B2 | 11/2007 | Cho et al. |
| 7,846,929 B2 | 12/2010 | Folkes et al. |
| 7,888,352 B2 | 2/2011 | Bayliss et al. |
| 8,367,663 B2 | 2/2013 | Cai et al. |
| 8,461,157 B2 | 6/2013 | Xiong et al. |
| 8,710,219 B2 | 4/2014 | Cai et al. |
| 8,906,909 B2 | 12/2014 | Cai et al. |
| 9,724,413 B2 | 8/2017 | Maecker et al. |
| 9,725,461 B2 | 8/2017 | Cai et al. |
| 10,336,770 B2 | 7/2019 | Cai et al. |
| 11,234,986 B2 * | 2/2022 | Wang ...................... A61P 35/04 |
| 2007/0249587 A1 | 10/2007 | Yonetoku et al. |
| 2008/0076768 A1 | 3/2008 | Chuckowree et al. |

(Continued)

FOREIGN PATENT DOCUMENTS

| | | |
|---|---|---|
| EP | 1277738 A1 | 1/2003 |
| WO | 03075929 A1 | 9/2003 |

(Continued)

OTHER PUBLICATIONS

"PI3 Kinase Signaling in Disease, CURIS News Release. Curis Presents Preclinical Data for CU-903 at Keystone Symposia Event," Drugs.com, <http://www.drugs.com/clinical_trials/curis-presents-preclinical-data-cu-903-keystone-symposiaevent-8220-pi3-kinase-signaling-8221-7094, 2009, 1-2.

(Continued)

*Primary Examiner* — Clinton A Brooks
*Assistant Examiner* — Kyle Nottingham
(74) *Attorney, Agent, or Firm* — Elmore Patent Law Group, P.C.; Edgar W. Harian; Carolyn S. Elmore

(57) ABSTRACT

The invention provides a method of treating cancer in a subject in need thereof, comprising administering to the subject:
(a) a compound of Formula I:

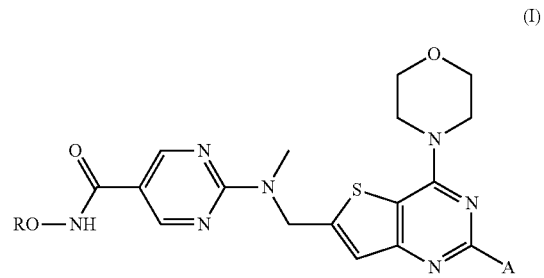

or a pharmaceutically acceptable salt thereof, wherein R is hydrogen or an acyl group; and
(b) a PD-1 signaling inhibitor; wherein the compound of Formula I or pharmaceutically acceptable salt thereof and the PD-1 signaling inhibitor are administered in amounts which in combination are therapeutically effective. The invention further provides a pharmaceutical composition comprising a compound of Formula I or a pharmaceutically acceptable salt thereof, a PD-1 signaling inhibitor and a pharmaceutically acceptable carrier or excipient.

9 Claims, 2 Drawing Sheets

(56) References Cited

U.S. PATENT DOCUMENTS

| | | |
|---|---|---|
| 2008/0076774 A1 | 3/2008 | Anand et al. |
| 2008/0125440 A1 | 5/2008 | Cai et al. |
| 2008/0125478 A1 | 5/2008 | Cai et al. |
| 2008/0139590 A1 | 6/2008 | Qian et al. |
| 2008/0161320 A1 | 7/2008 | Cai et al. |
| 2008/0194578 A1 | 8/2008 | Qian et al. |
| 2008/0221132 A1 | 9/2008 | Cai et al. |
| 2008/0234332 A1 | 9/2008 | Cai et al. |
| 2008/0242665 A1 | 10/2008 | Bayliss et al. |
| 2008/0269210 A1 | 10/2008 | Castanedo et al. |
| 2009/0076044 A1 | 3/2009 | Qian et al. |
| 2009/0093507 A1 | 4/2009 | Qian et al. |
| 2010/0102595 A1 | 4/2010 | Baumbarger |
| 2010/0222343 A1 | 9/2010 | Cai et al. |
| 2010/0233164 A1 | 9/2010 | Ebens, Jr. et al. |
| 2010/0292468 A1 | 11/2010 | Babu et al. |
| 2011/0086837 A1 | 4/2011 | Belvin et al. |
| 2012/0039906 A1 | 2/2012 | Olive |
| 2012/0088764 A1 | 4/2012 | Cai et al. |
| 2013/0102595 A1 | 4/2013 | Bao et al. |
| 2018/0133223 A1 | 5/2018 | Fattaey et al. |

FOREIGN PATENT DOCUMENTS

| | | |
|---|---|---|
| WO | 03076395 A1 | 9/2003 |
| WO | 03076400 A1 | 9/2003 |
| WO | 03076401 A1 | 9/2003 |
| WO | 03076421 A1 | 9/2003 |
| WO | 03076422 A1 | 9/2003 |
| WO | 2004017950 A2 | 3/2004 |
| WO | 2005097747 A1 | 10/2005 |
| WO | 2006046031 A1 | 5/2006 |
| WO | 2006046035 A1 | 5/2006 |
| WO | 2006046040 A1 | 5/2006 |
| WO | 2006082428 A2 | 8/2006 |
| WO | 2007082873 A1 | 7/2007 |
| WO | 2007082874 A1 | 7/2007 |
| WO | 2007082880 A1 | 7/2007 |
| WO | 2007127175 A2 | 11/2007 |
| WO | 2007127183 A1 | 11/2007 |
| WO | 2007129161 A2 | 11/2007 |
| WO | 2007113364 A1 | 11/2007 |
| WO | 2008033747 A2 | 3/2008 |
| WO | 2008055068 A2 | 5/2008 |
| WO | 2008070740 A1 | 6/2008 |
| WO | 2008073785 A2 | 6/2008 |
| WO | 2008100985 A2 | 8/2008 |
| WO | 2009036020 A1 | 3/2009 |
| WO | 2009036057 A1 | 3/2009 |
| WO | 2009036066 A1 | 3/2009 |
| WO | 2009036082 A2 | 3/2009 |
| WO | 2009042646 A1 | 4/2009 |
| WO | 2009055730 A1 | 4/2009 |
| WO | 2009058895 A1 | 5/2009 |
| WO | 2009086012 A1 | 7/2009 |
| WO | 2009155659 A1 | 12/2009 |
| WO | 2010008847 A2 | 1/2010 |
| WO | 2010105008 A2 | 9/2010 |
| WO | 2011054620 A1 | 5/2011 |
| WO | 2011130628 A1 | 10/2011 |
| WO | 2013019906 A1 | 2/2013 |
| WO | 2016210108 A1 | 12/2016 |
| WO | 2017223422 A1 | 12/2017 |
| WO | 2018073754 A1 | 4/2018 |

OTHER PUBLICATIONS

Belvin, M. et al., "PI3K inhibition rescues resistance to EGFR inhibitors in K-Ras mutant and ErbB3 expressing NSCLC cells", Poster No. 4004, AACR Apr. 2008, Poster Section 29, Board 2.
Bundgaard, H. "Design of Prodrugs: Bioreversible derivatives for various functional groups and chenmical entitites", Hans Bundgaard: "Design of Prodrugs", Elsevier, Amsterdam, New York, Oxford; Chapter 1, 1985.
Butler, L. M. et al., "Suberoylanilide Hydroxamic Acid, an Inhibitor of Histone Deacetylase, Suppresses the Growth of Prostate Cancer Cells in Vitro and in Vivo", Cancer Research, 60, 2000, 5165-5170.
Chaussade, C. et al., "Evidence for functional redundancy of class IA PI3K isoforms in insulin signalling", Biochem. J., 404, 2007, 449-458.
Csordas, "On the biological role of histone acetylation, Review Article", Biochem. J., 265, 1990, 23-38.
Curtin, M. et al., "Histone Deacetylase Inhibitors: The Abbott Experience", Current Medicinal Chemistry, 10, 2003, 2373-2392.
Engelman, J. A. et al., "Targeting PI3K signalling in cancer: opportunities, challenges and limitations", Nature Reviews Cancer, 9, 2009, 550-562.
Fan, Q-W et al., "A Dual Phosphoinositide-3-Kinase $\alpha$/mTOR Inhibitor Cooperates with Blockade of Epidermal Growth Factor Receptor in PTEN-Mutant Glioma", Cancer Res., 67(17), 2007, 7960-7965.
Fan, Q-W et al., "A dual PI3 kinase/mTOR inhibitor reveals emergent efficacy in glioma", Cancer Cell, 9, 2006, 341-349.
Fieser, L. et al., Reagents for Organic Synthesis, vol. 1, Wiley: NY, Pub Date Discrepancy, 1974, 723-730.
Folkes, et al., "The Identification of 2-(1H-Indazol-4-yl)-6-(4-methanesulfonyl-piperazin-1-ylmethyl)-4-morpholin-4-yl-thieno[3,2-d]pyrimidine (GDC-0941) as a Potent, Selective, Orally Bioavailable Inhibitor of Class I PI3 Kinase for the Treatment of Cancer", J. Medic. Chem., 51, 2008, 5522-5532.
Folkman, et al., "Tumor Angiogenesis", Adv. Cancer Res., vol. 43, 1985, 175-203.
Greene, T. W et al., Protective Groups in Organic Synthesis, John Wiley & Sons: NY, 1982, 218-220, 224, 251.
Hayakawa, M. et al., "Synthesis and biological evaluation of 4-morpholino-2-phenylquinazolines and related derivatives as novel PI3 kinase p110$\alpha$ inhibitors", Bioorganic & Medicinal Chemistry, 14, 2006, 6847-6858.
Hayakawa, M. et al., "Synthesis and biological evaluation of imidazo[1,2-a]pyridine derivatives as novel PI3 kinase p110$\alpha$ inhibitors", Bioorganic & Medicinal Chemistry, 15, <! MISCELLANEOUS** > 2007, 403-412.
Krogsgaard-Larsen, et al., (ed.) Design and Application of Prodrugs, Textbook of Drug Design and Development, Chapter 5, 1991, 113-191.
Kulp, S. K. "Antitumor Effects of a Novel Phenylbutyrate-Based Histone Deacetylase Inhibitor, (S)-HDAC-42, in Prostate Cancer", Clinical Cancer Research, 12(17), 2006, 5199-5206.
Lindmo, et al., "Regulation of membrane traffic by phosphoinositide 3-kinases", J. Cell Sci., 119, 2006, 605-614.
Mayo, M. W. et al., "Ineffectiveness of Histone Deacetylase Inhibitors to Induce Apoptosis Involves the Transcriptional Activation of NF-$\kappa$B through the Akt Pathway", The Journal of Biological Chemistry, 278(21), 2003, 18980-18989.
Minucci, S. et al., "Histone deacetylase inhibitors and the promise of epigenetic (and more) treatments for cancer", Nature, 6, 2006, 38-51.
Nielsen, N. M. et al., "Glycolamide Esters as Biolabile Prodrugs of Carboxylic Acid Agents: Synthesis, Stability, Bioconversion, and Physicochemical Properties", J. of Pharmaceutical Sciences, 77(4): 285-298 (1988).
Ozaki, K-I et al., "Blockade of the ERK or PI3K-Akt signaling pathway enhances the cytotoxicity of histone deacetylase inhibitors in tumor cells resistant to gefitinib or imatinib", Biochemical and biophysical research communications, 391(4), 2010, 1610-1615.
Schirrmacher, V. et al., "Workshop: active specific immunotherapy with tumor cell vaccines", J. Cancer Res. Clin. Oncol. 121, 1995, 487.
Stephens, L. et al., "Phosphoinositide 3-kinases as drug targets in cancer", Current Opinion in Pharmacology, 5(4), 2005, 357-365.
Suzuki, T. et al., "Novel Histone Deacetylase Inhibitors: Design, Synthesis, Enzyme Inhibition, and Binding Mode Study of SAHA-Based Non-hydroxamates", Bioorganic & Medicinal Chemistry Letters, 13, 2003, 4321-4326.

(56) References Cited

OTHER PUBLICATIONS

Taunton, J. et al., "A Mammalian Histone Deacetylase Related to the Yeast Transciptional Regulator Rpd3p", Science, 272, 1996, 408-411.

Wegener, D. et al., "Identification of novel small-molecule histone deacetylase inhibitors by medium-throughput screening using a fluorigenic assay", Biochem. Journal, 413, 2008, 143-150.

Wozniak, M. B. et al., "Vorinostat interferes with the signaling transduction pathway of T-cell receptor and synergizes with phosphoinositide-3 kinase inhibitors in cutaneous T-cell lymphoma", Haematologica, 95(4), 2010, 613-621.

Yaguchi, S. I. et al., "Antitumor Activity of ZSTK474, a New Phosphatidylinositol 3-Kinase Inhibitor", Journal of the National Cancer Institute, 98(8), 2006, 545-556.

Fruman, D. A. et al., "The PI3K Pathway in Human Disease", Cell, 170(4), doi.org/10.1016/j.cell.2017.07.029, Aug. 10, 2017, 605-635.

Zhao, L. et al., "A blockade of PD-L1 produced antitumor and antimetastatic effects in an orthotopic mouse pancreatic cancer model via the PI3K/Akt/mTOR signaling pathway", Onco Targets Ther., 2017(10), doi: 10.2147/OTT.S130481, Apr. 12, 2017, 2115-2126.

\* cited by examiner

COMBINATION THERAPY WITH A PHOSPHOINOSITIDE 3-KINASE INHIBITOR WITH A ZINC BINDING MOIETY

RELATED APPLICATIONS

This application is a continuation of U.S. application Ser. No. 16/565,921, filed Sep. 10, 2019, which claims the benefit of U.S. Provisional Application No. 62/729,648, filed on Sep. 11, 2018. The entire teachings of the above applications are incorporated herein by reference.

BACKGROUND OF THE INVENTION

Therapeutic regimens for the treatment of cancers often involve combination therapy with two or more agents. In particular, target therapies may be combined to more effectively treat various types of cancer and inhibit the development of cancer cells resistant to therapy. There is a need in the field of cancer drug development for particularly effective combinations of drugs for the treatment of specific types of cancer.

SUMMARY OF THE INVENTION

The present invention relates to a combination therapy with a compound of Formula I,

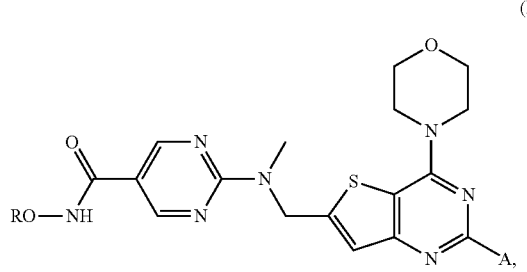

(I)

or a pharmaceutically acceptable salt thereof, where R is hydrogen or an acyl group. The acyl group is preferably $R_1C(O)-$, where $R_1$ is substituted or unsubstituted $C_1$-$C_{24}$-alkyl, preferably $C_1$-$C_{10}$-alkyl, and more preferably $C_1$-$C_6$-alkyl; substituted or unsubstituted $C_2$-$C_{24}$-alkenyl, preferably $C_2$-$C_{10}$-alkenyl, and more preferably $C_2$-$C_6$-alkenyl; substituted or unsubstituted $C_2$-$C_{24}$-alkynyl, preferably $C_2$-$C_{10}$-alkynyl, and more preferably $C_2$-$C_6$-alkynyl; substituted or unsubstituted aryl, preferably substituted or unsubstituted phenyl; or substituted or unsubstituted heteroaryl, and A is optionally substituted phenyl, optionally substituted pyridyl or optionally substituted pyrimidyl; and a PD-1 signaling inhibitor for the treatment of cancers. For example, in one embodiment, the invention provides a method of preventing or treating cancer in a subject in need thereof. The method comprises administering to the subject a compound of Formula I, or a pharmaceutically acceptable salt thereof, and a PD-1 signaling inhibitor, wherein the compound of Formula I and the PD-1 signaling inhibitor are administered in amounts which in combination are therapeutically effective. Preferably, the compound of Formula I or salt thereof and the PD-1 signaling inhibitor are administered to the subject in amounts which are synergistic.

The invention also relates to pharmaceutical compositions comprising a compound of Formula I, or a pharmaceutically acceptable salt thereof, in combination with a PD-1 signaling inhibitor and a pharmaceutically acceptable excipient or carrier.

The compounds of Formula I and, in particular, the compound of Formula I wherein R is hydrogen and A is 2-methoxy-5-pyridyl, also referred to herein as Compound 1, have advantageous properties for use as therapeutic agents, such as for the treatment of cancers and other diseases and disorders associated with PI3 kinase activity and/or HDAC activity. Compound 1, for example, has potent inhibitory activity against the molecular targets PI3K and HDAC and potent antiproliferative activity against a variety of cancer cell lines in vitro. Compound 1 has significant oral bioavailability as observed in animal models. Upon either oral or intravenous dosing in xenograft tumor bearing mice, the compound shows significant uptake by the tumor tissue and pharmacodynamic activity in tumor tissue. Compound 1 also shows substantial antitumor activity in mouse xenograft tumor models following either oral or intravenous administration. The compound also has a favorable safety profile, as shown, for example, by genotoxicity testing using the Ames test.

BRIEF DESCRIPTION OF THE DRAWINGS

The foregoing and other objects, features and advantages of the invention will be apparent from the following more particular description of preferred embodiments of the invention, as illustrated in the accompanying drawings.

DETAILED DESCRIPTION OF THE INVENTION

Figure 1:
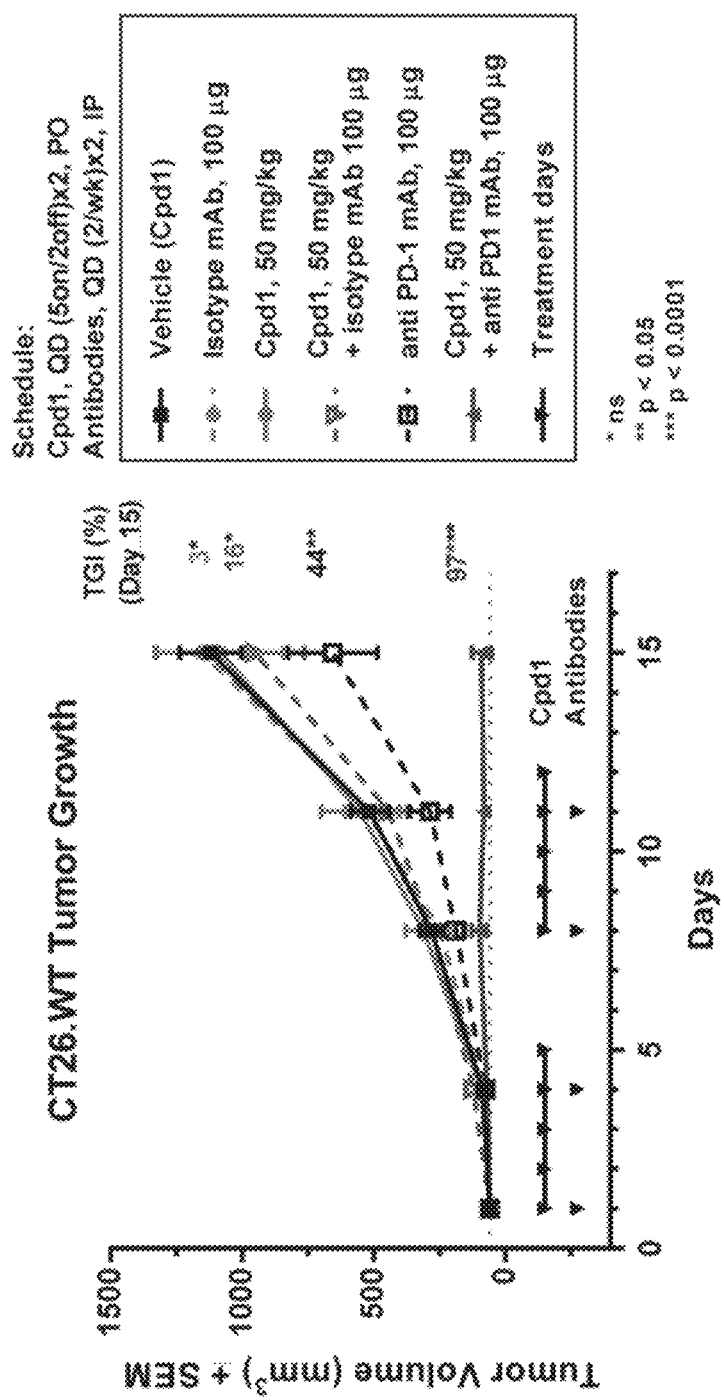
FIG. 1 is a graph of tumor volume versus time in the mouse CT26.WT xenograft model as described in Example 11.

The present invention relates to methods and compositions for combination therapy for cancer comprising a compound of Formula I or a pharmaceutically acceptable salt thereof and a PD-1 signaling inhibitor. In a preferred embodiment of the compounds of Formula I, A is phenyl, pyridyl or pyrimidyl substituted with methoxy, amino or N-methylamino. More preferably, A is one of the groups set forth below.

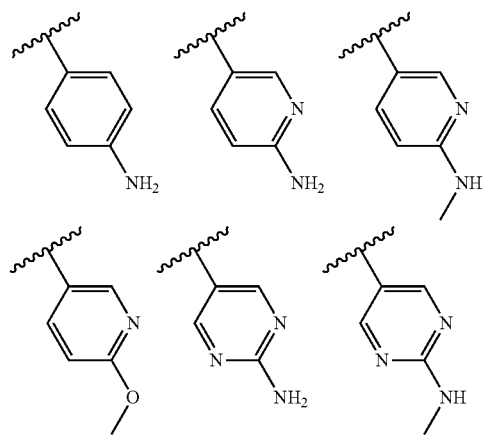

-continued

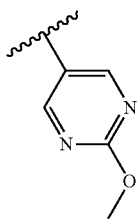

In certain embodiments of the compounds of Formula I, A is one of the groups shown above and R is hydrogen.

In a preferred embodiment, the compound of Formula I is selected from Compounds 1, 2 and 3 below and pharmaceutically acceptable salts thereof.

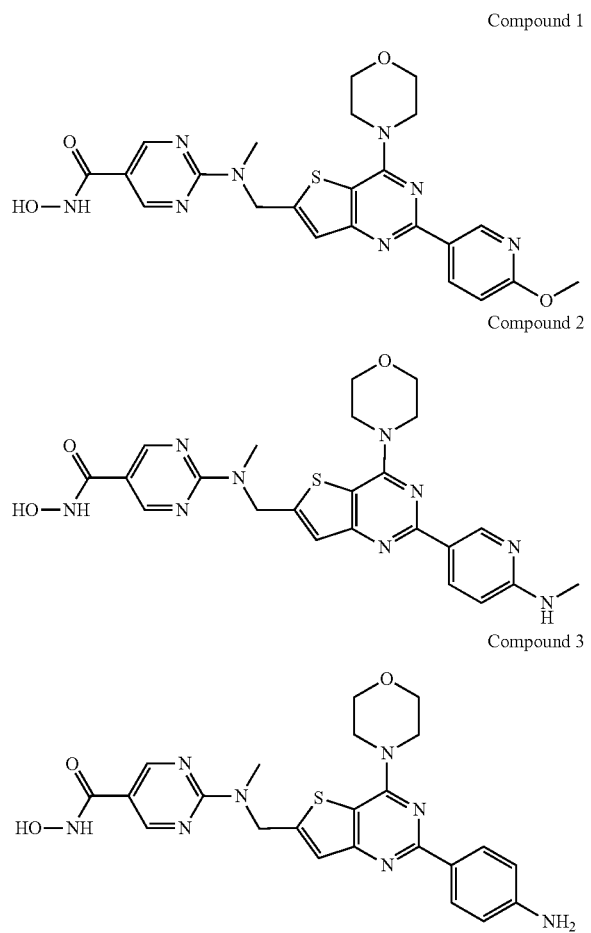

The invention provides a method for the preventing or treating cancer in a subject in need thereof. The method comprises the step of administering to the subject the compound of Formula I or a pharmaceutically acceptable salt thereof and a PD-1 signaling inhibitor, wherein the compound of Formula I or pharmaceutically acceptable salt thereof and the PD-1 signaling inhibitor are administered in amounts which in combination are therapeutically effective.

The PD-1 signaling inhibitor can be any compound which inhibits PD-1 signaling. For example, the PD-1 signaling inhibitor can inhibit PD-1 and or an activating ligand of PD-1, such as PD-L1 or PD-L2. The PD-1 signaling inhibitor can be a small molecule, a polynucleotide or a protein, such as an antibody. Preferably, the PD-1 signaling inhibitor is a monoclonal antibody, more preferably a humanized or fully human monoclonal antibody. In one embodiment, the PD-1 signaling inhibitor is an anti-PD-1 monoclonal antibody. In another embodiment, the PD-1 signaling inhibitor is an anti-PD-L1 monoclonal antibody. In another embodiment, the PD-1 signaling inhibitor is an anti-PD-L2 monoclonal antibody. Suitable PD-1 signaling inhibitors include, but are not limited to, those described in U.S. Pat. No. 8,008,449, WO 2006/121168, WO 2009/114335, U.S. Pat. Nos. 8,354,509, 8,609,089, US 2010/0028330, US 2012/0114649, WO 2007/005874, WO 2010/077634, U.S. Pat. No. 7,943,743, US 2012/0039906 and WO/2011/066342, each of which is incorporated herein in its entirety. Examples of suitable PD-1 signaling inhibitors include YW243.55.S70, MPDL3280A, MEDI-4736, MSB-0010718C, MDX-1105, and AMP-224. Preferred PD-1 signaling inhibitors include pembrolizumab (KEYTRUDA™), nivolumab (OPDIVO™), atelolizumab (TECENTRIQ™), avelumab (BAVENCIO™), durvalumab (IMFINZI™), and pidilizumab.

In particularly preferred embodiments of the methods and compositions of the invention, the compound of Formula I is Compound 1.

In particularly preferred embodiments of the invention, the PD-1 signaling inhibitor is pembrolizumab or nivolumab.

In certain embodiments of the method of the invention, the compound of Formula I or pharmaceutically acceptable salt thereof and the PD-1 signaling inhibitor are administered simultaneously to the subject as separate compositions. In certain embodiments, the compound of Formula I or a pharmaceutically acceptable salt thereof and the PD-1 signaling inhibitor are administered simultaneously to the subject via the same or different routes of administration.

In certain embodiments, the compound of Formula I or a pharmaceutically acceptable salt thereof and the PD-1 signaling inhibitor are administered sequentially to the subject as separate compositions. In certain embodiments, the compound of Formula I and the PD-1 signaling inhibitor are administered sequentially to the subject via the same or different routes of administration. In one embodiment, the PD-1 signaling inhibitor is administered to the subject after administering the compound of Formula I or pharmaceutically acceptable salt thereof to the subject. In another embodiment, the PD-1 signaling inhibitor is administered to the subject before administering the compound of Formula I or pharmaceutically acceptable salt thereof to the subject.

In certain embodiments in which the compound of Formula I or pharmaceutically acceptable salt thereof and the PD-1 signaling inhibitor are administered as separate compositions, and each composition is independently administered transmucosally, orally, rectally, vaginally, sublingually, intravenously, intramuscularly, subcutaneously, bucally, intranasally, intracisternally, intraperitoneally, or intra-aurally. In certain embodiments, one or both compositions is administered in a suppository or hydrogel. In preferred embodiments, both compositions are administered orally.

In certain embodiments in which the compound of Formula I or pharmaceutically acceptable salt thereof and the PD-1 signaling inhibitor are administered as separate compositions, the timing of their administration is such that the pharmacological activities of the agents overlap in time, thereby exerting a combined therapeutic effect. For example, the compound of Formula I or pharmaceutically acceptable salt thereof and the PD-1 signaling inhibitor can be administered sequentially with a time separation of more than about 60 minutes. For example, the time between the sequential administration of the compound of Formula I or pharmaceutically acceptable salt thereof and the PD-1 signaling inhibitor can be more than 60 minutes, more than 2 hours, more than 5 hours, more than 10 hours, more than 1 day, more than 2 days, more than 3 days, or more than 1 week apart. The optimal administration times will depend on the rates of absorption, distribution, metabolism and/or excretion of the compound of Formula I or pharmaceutically acceptable salt thereof and the PD-1 signaling inhibitor.

Either the compound of Formula I or pharmaceutically acceptable salt thereof or the PD-1 signaling inhibitor can be administered first. For example, the PD-1 signaling inhibitor can be administered to the subject after the time at which the compound of Formula I or pharmaceutically acceptable salt thereof is administered. In this case, it can be desirable to administer the PD-1 signaling inhibitor prior to the time at which about 50% (e.g., prior to the time at which about 40%, about 30%, about 20%, about 10%, or about 5%) of the compound of Formula I is metabolized or excreted by the subject. In another example, a first dose of the compound of Formula I or pharmaceutically acceptable salt thereof is administered to the subject, followed by administration of a single dose of the PD-1 signaling inhibitor, which is then followed by an additional dose of the compound of Formula I or pharmaceutically acceptable salt thereof.

In certain embodiments, the compound of Formula I or pharmaceutically acceptable salt thereof and the PD-1 signaling inhibitor are administered in a single dosage form, which is administered transmucosally, orally, rectally, vaginally, sublingually, intravenously, intramuscularly, subcutaneously bucally, intranasally, intracisternally, intraperitoneally, or intra-aurally. Preferably, the single dosage form is administered orally.

The compound of Formula I may be administered about once per week, about once per day, or more than once daily. In an embodiment, the compound of Formula I or pharmaceutically acceptable salt thereof is administered orally. In another embodiment, the compound of Formula I or pharmaceutically acceptable salt thereof is administered parenterally, for example, intravenously. The compound of Formula I or pharmaceutically acceptable salt thereof may be administered at a daily dose of about 1 mg to about 1,500 mg. For example, the compound of Formula I or pharmaceutically acceptable salt thereof may be administered at a daily dose of about 200 mg. In one embodiment, the compound of Formula I or pharmaceutically acceptable salt thereof is administered at a dosage of about 1 mg to about 250 mg per kg of body weight.

It will be understood, however, that the dose frequency and total daily dose of the compound of Formula I or pharmaceutically acceptable salt thereof and the PD-1 signaling inhibitor can be determined for an individual patient by one of skill in the art, for example, by the attending physician within the scope of sound medical judgment. The specific dose or doses for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The term "cancer" refers to any cancer caused by the proliferation of malignant neoplastic cells, such as tumors, neoplasms, carcinomas, sarcomas, leukemias, lymphomas and the like. For example, cancers include, but are not limited to, mesothelioma, leukemias and lymphomas such as cutaneous T-cell lymphomas (CTCL), noncutaneous peripheral T-cell lymphomas, lymphomas associated with human T-cell lymphotrophic virus (HTLV) such as adult T-cell leukemia/lymphoma (ATLL), B-cell lymphoma, such as diffuse large B-cell lymphoma (DLBCL), acute nonlymphocytic leukemias, chronic lymphocytic leukemia, chronic myelogenous leukemia, acute myelogenous leukemia, lymphomas, and multiple myeloma, non-Hodgkin lymphoma, acute lymphatic leukemia (ALL), chronic lymphatic leukemia (CLL), Hodgkin's lymphoma, Burkitt lymphoma, adult T-cell leukemia lymphoma, acute-myeloid leukemia (AML), chronic myeloid leukemia (CML), or hepatocellular carcinoma. Further examples include myelodisplastic syndrome, childhood solid tumors such as brain tumors, neuroblastoma, retinoblastoma, Wilms' tumor, bone tumors, and soft-tissue sarcomas, common solid tumors of adults such as head and neck cancers (e.g., oral, laryngeal, nasopharyngeal and esophageal), genitourinary cancers (e.g., prostate, bladder, renal, uterine, ovarian, testicular), lung cancer (e.g., small-cell and nonsmall-cell), breast cancer, pancreatic cancer, melanoma and other skin cancers, stomach cancer, brain tumors, tumors related to Gorlin's syndrome (e.g., medulloblastoma, meningioma, etc.), and liver cancer. Additional exemplary forms of cancer which may be treated by the subject compounds include, but are not limited to, cancer of skeletal or smooth muscle, stomach cancer, cancer of the small intestine, rectum carcinoma, cancer of the salivary gland, endometrial cancer, adrenal cancer, anal cancer, rectal cancer, parathyroid cancer, and pituitary cancer.

Additional cancers that the compounds described herein may be useful in preventing, treating and studying are, for example, colon carcinoma, familial adenomatous polyposis carcinoma and hereditary non-polyposis colorectal cancer, or melanoma. Further, cancers include, but are not limited to, labial carcinoma, larynx carcinoma, hypopharynx carcinoma, tongue carcinoma, salivary gland carcinoma, gastric carcinoma, adenocarcinoma, thyroid cancer (medullary and papillary thyroid carcinoma), renal carcinoma, kidney parenchyma carcinoma, cervix carcinoma, uterine corpus carcinoma, endometrium carcinoma, chorion carcinoma, testis carcinoma, urinary carcinoma, melanoma, brain tumors such as glioblastoma, astrocytoma, meningioma, medulloblastoma and peripheral neuroectodermal tumors, gall bladder carcinoma, bronchial carcinoma, multiple myeloma, basalioma, teratoma, retinoblastoma, choroidea melanoma, seminoma, rhabdomyosarcoma, craniopharyngeoma, osteosarcoma, chondrosarcoma, myosarcoma, liposarcoma, fibrosarcoma, Ewing sarcoma, and plasmocytoma. In one aspect of the invention, the present invention provides for the use of one or more compounds of the invention in the manufacture of a medicament for the treatment of cancer.

In one embodiment, the cancer to be treated is a hematological cancer. Hematological cancers include leukemias, lymphomas and multiple myeloma. Examples include lymphocytic leukemias, such as acute lymphocytic leukemia, including precursor B acute lymphoblastic leukemia, precursor T acute lymphoblastic leukemia, Burkitt's leukemia, and acute biphenotypic leukemia; and chronic lymphocytic leukemia, including B-cell prolymphocytic leukemia; and myelogenous leukemias, such as acute myologenous leukemia, including acute promyelocytic leukemia, acute myeloblastic leukemia, and acute megakaryoblastic leukemia; and chronic myologenous leukemia, including chronic monocytic leukemia; acute monocytic leukemia. Other leukemias include hairy cell leukemia; T-cell prolymphocytic leukemia; large granular lymphocytic leukemia; and Adult T-cell leukemia.

Lymphomas include Hodgkin's lymphoma and Non-Hodgkin's lymphoma, including B-cell lymphomas, T cell lymphomas, NK cell lymphomas and precursor lymphoid neoplasms. B cell lymphomas include Burkitt lymphoma/leukemia, diffuse large B cell lymphoma, B-cell chronic lymphocytic leukemia/small cell lymphoma, B-cell prolymphocytic leukemia, Lymphoplasmacytic lymphoma (such as Waldenström macroglobulinemia), Splenic marginal zone lymphoma, Hairy cell leukemia, Plasma cell neoplasms, Plasma cell myeloma (also known as multiple myeloma), Plasmacytoma, Monoclonal immunoglobulin deposition diseases, Heavy chain diseases, Extranodal marginal zone B cell lymphoma, also called MALT lymphoma, Nodal marginal zone B cell lymphoma, Follicular lymphoma, Primary cutaneous follicle center lymphoma, Mantle cell lymphoma, Lymphomatoid granulomatosis, Primary mediastinal (thymic) large B-cell lymphoma, Intravascular large B-cell lymphoma, ALK+ large B-cell lymphoma, Plasmablastic lymphoma, Primary effusion lymphoma, Large B-cell lymphoma arising in HHV8-associated multicentric Castleman's disease, Lymphomatoid granulomatosis, Primary mediastinal (thymic) large B-cell lymphoma, Intravascular large B-cell lymphoma, ALK+ large B-cell lymphoma, Plasmablastic lymphoma, Primary effusion lymphoma, and Large B-cell lymphoma arising in HHV8-associated multicentric Castleman's disease.

T-cell and NK cell lymphomas include cutaneous T-cell, T-cell prolymphocytic leukemia, T-cell large granular lymphocyte leukemia, Aggressive NK cell leukemia, Adult T-cell leukemia/lymphoma, Extranodal NK/T-cell lymphoma, nasal type, Enteropathy-associated T-cell lymphoma, Hepatosplenic T-cell lymphoma, Blastic NK cell lymphoma, Mycosis fungoides/Sezary syndrome, Primary cutaneous CD30-positive T cell lymphoproliferative disorders, such as Primary cutaneous anaplastic large cell lymphoma, Lymphomatoid papulosis, Peripheral T-cell lymphoma not otherwise specified, Angioimmunoblastic T cell lymphoma, and Anaplastic large cell lymphoma.

In preferred embodiments, the cancer to be treated is non-Hodgkins lymphoma and, more preferably, a B cell lymphoma. In particularly preferred embodiments, the cancer to be treated is a diffuse large B cell lymphoma (DLBCL), for example a DLBCL of the ABC subtype, DLBCL of the GCB subtype, double hit DLBCL or double expresser DLBCL (Quintanilla-Martinez, L., *Hematol. Oncol.* 2015, 33:50-55). In certain embodiments, the cancer is relapsed or refractory DLBCL.

In one embodiment, the present invention provides the use of a compound of Formula I or a pharmaceutically acceptable salt thereof in the manufacture of a medicament for the treatment of cancer in combination with a PD-1 signaling inhibitor. In another embodiment, the present invention provides the use of a compound of Formula I or a pharmaceutically acceptable salt thereof and a PD-1 signaling inhibitor in the manufacture of a medicament for treating cancer. In a preferred embodiment, the compound of Formula I is Compound 1 or a pharmaceutically acceptable salt thereof, and the PD-1 signaling inhibitor is pembrolizumab or nivolumab.

The invention further encompasses pharmaceutical compositions comprising a compound of Formula I or a pharmaceutically acceptable salt thereof, and a PD-1 signaling inhibitor. In one embodiment, the compound of Formula I is Compound 1, Compound 2 or Compound 3, and the PD-1 signaling inhibitor is pembrolizumab or nivolumab.

The compound of Formula I or pharmaceutically acceptable salt thereof and the PD-1 signaling inhibitor can be administered by any suitable means, including, without limitation, parenteral, intravenous, intramuscular, subcutaneous, implantation, oral, sublingual, buccal, nasal, pulmonary, transdermal, topical, vaginal, rectal, and transmucosal administrations or the like. Topical administration can also involve the use of transdermal administration such as transdermal patches or iontophoresis devices. Pharmaceutical preparations include a solid, semisolid or liquid preparation (tablet, pellet, troche, capsule, suppository, cream, ointment, aerosol, powder, liquid, emulsion, suspension, syrup, injection, etc.) containing a compound of Formula I or a pharmaceutically acceptable salt thereof, a PD-1 signaling inhibitor, or both which is suitable for selected mode of administration. In one embodiment, the pharmaceutical compositions are administered orally, and are thus formulated in a form suitable for oral administration, i.e., as a solid or a liquid preparation. Suitable solid oral formulations include tablets, capsules, pills, granules, pellets, sachets and effervescent, powders, and the like. Suitable liquid oral formulations include solutions, suspensions, dispersions, emulsions, oils and the like. In one embodiment of the present invention, the composition is formulated in a capsule. In accordance with this embodiment, the compositions of the present invention comprise in addition to the active compound and the inert carrier or diluent, a hard gelatin capsule.

Any inert excipient that is commonly used as a carrier or diluent may be used in the formulations of the present invention, such as for example, a gum, a starch, a sugar, a cellulosic material, an acrylate, or mixtures thereof. A preferred diluent is microcrystalline cellulose. The compositions may further comprise a disintegrating agent (e.g., croscarmellose sodium) and a lubricant (e.g., magnesium stearate), and may additionally comprise one or more additives selected from a binder, a buffer, a protease inhibitor, a surfactant, a solubilizing agent, a plasticizer, an emulsifier, a stabilizing agent, a viscosity increasing agent, a sweetener, a film forming agent, or any combination thereof. Furthermore, the compositions of the present invention may be in the form of controlled release or immediate release formulations.

For liquid formulations, pharmaceutically acceptable carriers may be aqueous or non-aqueous solutions, suspensions, emulsions or oils. Examples of non-aqueous solvents are propylene glycol, polyethylene glycol, and injectable organic esters such as ethyl oleate. Aqueous carriers include water, alcoholic/aqueous solutions, emulsions or suspensions, including saline and buffered media. Examples of oils are those of petroleum, animal, vegetable, or synthetic origin, for example, peanut oil, soybean oil, mineral oil, olive oil, sunflower oil, and fish-liver oil. Solutions or suspensions can also include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid (EDTA); buffers such as acetates, citrates or phosphates, and agents for the adjustment of tonicity such as sodium chloride or dextrose. The pH can be adjusted with acids or bases, such as hydrochloric acid or sodium hydroxide.

In addition, the compositions may further comprise binders (e.g., acacia, cornstarch, gelatin, carbomer, ethyl cellulose, guar gum, hydroxypropyl cellulose, hydroxypropyl methyl cellulose, povidone), disintegrating agents (e.g., cornstarch, potato starch, alginic acid, silicon dioxide, croscarmellose sodium, crospovidone, guar gum, sodium starch glycolate, Primogel), buffers (e.g., tris-HCI., acetate, phosphate) of various pH and ionic strength, additives such as albumin or gelatin to prevent absorption to surfaces, detergents (e.g., Tween 20, Tween 80, Pluronic F68, bile acid salts), protease inhibitors, surfactants (e.g., sodium lauryl sulfate), permeation enhancers, solubilizing agents (e.g., glycerol, polyethylene glycerol, polyethylene glycol), a glidant (e.g., colloidal silicon dioxide), anti-oxidants (e.g., ascorbic acid, sodium metabisulfite, butylated hydroxyanisole), stabilizers (e.g., hydroxypropyl cellulose, hydroxypropylmethyl cellulose), viscosity increasing agents (e.g., carbomer, colloidal silicon dioxide, ethyl cellulose, guar gum), sweeteners (e.g., sucrose, aspartame, citric acid), flavoring agents (e.g., peppermint, methyl salicylate, or orange flavoring), preservatives (e.g., Thimerosal, benzyl alcohol, parabens), lubricants (e.g., stearic acid, magnesium stearate, polyethylene glycol, sodium lauryl sulfate), flowaids (e.g., colloidal silicon dioxide), plasticizers (e.g., diethyl phthalate, triethyl citrate), emulsifiers (e.g., carbomer, hydroxypropyl cellulose, sodium lauryl sulfate), polymer coatings (e.g., poloxamers or poloxamines), coating and film forming agents (e.g., ethyl cellulose, acrylates, polymethacrylates) and/or adjuvants.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions can also be used as pharmaceutically acceptable carriers. These can be prepared according to methods known to those skilled in the art, for example, as described in U.S. Pat. No. 4,522,811.

It is especially advantageous to formulate oral compositions in unit dosage form for ease of administration and uniformity of dosage. "Unit dosage form", as used herein, refers to physically discrete units suited as unitary dosages for the subject to be treated; each unit containing a predetermined quantity of active compound calculated to produce the desired therapeutic effect in association with the required pharmaceutical carrier. The specification for the unit dosage forms of the invention are dictated by and directly dependent on the unique characteristics of the active compound and the particular therapeutic effect to be achieved, and the limitations inherent in the art of compounding such an active compound for the treatment of individuals.

Formulations of the invention intended for oral administration can include one or more permeation enhancers, including long chain fatty acids or salts thereof, such as decanoic acid and sodium decanoate.

In one preferred embodiment, the compound can be formulated in an aqueous solution for intravenous injection. In one embodiment, solubilizing agents can be suitably employed. A particularly preferred solubilizing agent includes cyclodextrins and modified cyclodextrins, such as sulfonic acid substituted β-cyclodextrin derivative or salt thereof, including sulfobutyl derivatized-β-cyclodextrin, such as sulfobutylether-7-O-cyclodextrin which is sold by CyDex, Inc. under the tradename CAPTISOL®.

The pharmaceutical compositions can be included in a container, pack, or dispenser together with instructions for administration.

Daily administration may be repeated continuously for a period of several days to several years. Oral treatment may continue for between one week and the life of the patient. Preferably the administration may take place for five consecutive days after which time the patient can be evaluated to determine if further administration is required. The administration can be continuous or intermittent, e.g., treatment for a number of consecutive days followed by a rest period. The compounds of the present invention may be administered intravenously on the first day of treatment, with oral administration on the second day and all consecutive days thereafter.

The preparation of pharmaceutical compositions that contain an active component is well understood in the art, for example, by mixing, granulating, or tablet-forming processes. The active therapeutic ingredient is often mixed with excipients that are pharmaceutically acceptable and compatible with the active ingredient. For oral administration, the active agents are mixed with additives customary for this purpose, such as vehicles, stabilizers, or inert diluents, and converted by customary methods into suitable forms for administration, such as tablets, coated tablets, hard or soft gelatin capsules, aqueous, alcoholic or oily solutions and the like as detailed above.

The amount of the compound administered to the patient is less than an amount that would cause toxicity in the patient. In certain embodiments, the amount of the compound that is administered to the patient is less than the amount that causes a concentration of the compound in the patient's plasma to equal or exceed the toxic level of the compound. Preferably, the concentration of the compound in the patient's plasma is maintained at about 10 nM. In one embodiment, the concentration of the compound in the patient's plasma is maintained at about 25 nM. In one embodiment, the concentration of the compound in the patient's plasma is maintained at about 50 nM. In one embodiment, the concentration of the compound in the patient's plasma is maintained at about 100 nM. In one embodiment, the concentration of the compound in the patient's plasma is maintained at about 500 nM. In one embodiment, the concentration of the compound in the patient's plasma is maintained at about 1000 nM. In one embodiment, the concentration of the compound in the patient's plasma is maintained at about 2500 nM. In one embodiment, the concentration of the compound in the patient's plasma is maintained at about 5000 nM. The optimal amount of the compound that should be administered to the patient in the practice of the present invention will depend on the particular compound used and the type of cancer being treated.

Definitions

Listed below are definitions of various terms used to describe this invention. These definitions apply to the terms as they are used throughout this specification and claims, unless otherwise limited in specific instances, either individually or as part of a larger group.

The term "acyl" refers to hydrogen, alkyl, partially saturated or fully saturated cycloalkyl, partially saturated or fully saturated heterocycle, aryl, and heteroaryl substituted carbonyl groups. For example, acyl includes groups such as (C$_1$-C$_6$)alkanoyl (e.g., formyl, acetyl, propionyl, butyryl, valeryl, caproyl, t-butylacetyl, etc.), (C$_3$-C$_6$)cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions. When indicated as being "optionally substituted", the acyl group may be unsubstituted or optionally substituted with one or more substituents (typically, one to three substituents) independently selected from the group of substituents listed below in the definition for "substituted" or the alkyl, cycloalkyl, heterocycle, aryl and heteroaryl portion of the acyl group may be substituted as described above in the preferred and more preferred list of substituents, respectively.

The term "alkyl" embraces linear or branched radicals having one to about twenty carbon atoms or, preferably, one to about twelve carbon atoms. More preferred alkyl radicals are "lower alkyl" radicals having one to about ten carbon atoms. Most preferred are lower alkyl radicals having one to about eight carbon atoms. Examples of such radicals include methyl, ethyl, n-propyl, isopropyl, n-butyl, isobutyl, sec-butyl, tert-butyl, pentyl, iso-amyl, hexyl and the like.

The term "alkenyl" embraces linear or branched radicals having at least one carbon-carbon double bond of two to about twenty carbon atoms or, preferably, two to about twelve carbon atoms. More preferred alkenyl radicals are "lower alkenyl" radicals having two to about ten carbon atoms and more preferably about two to about eight carbon atoms. Examples of alkenyl radicals include ethenyl, allyl, propenyl, butenyl and 4-methylbutenyl. The terms "alkenyl", and "lower alkenyl", embrace radicals having "cis" and "trans" orientations, or alternatively, "E" and "Z" orientations.

The term "alkynyl" embraces linear or branched radicals having at least one carbon-carbon triple bond of two to about twenty carbon atoms or, preferably, two to about twelve carbon atoms. More preferred alkynyl radicals are "lower alkynyl" radicals having two to about ten carbon atoms and more preferably about two to about eight carbon atoms. Examples of alkynyl radicals include propargyl, 1-propynyl, 2-propynyl, 1-butyne, 2-butynyl and 1-pentynyl.

The term "aryl", alone or in combination, means a carbocyclic aromatic system containing one, two or three rings wherein such rings may be attached together in a pendent manner or may be fused. The term "aryl" embraces aromatic radicals such as phenyl, naphthyl, tetrahydronaphthyl, indane and biphenyl.

The term "heteroaryl" embraces unsaturated heterocyclyl radicals. Examples of heteroaryl radicals include unsaturated 3 to 6-membered, preferably 5 or 6-membered, heteromonocyclic group containing 1 to 4 nitrogen atoms, for example, pyrrolyl, pyrrolinyl, imidazolyl, pyrazolyl, pyridyl, pyrimidyl, pyrazinyl, pyridazinyl, triazolyl (e.g., 4H-1,2,4-triazolyl, 1H-1,2,3-triazolyl, 2H-1,2,3-triazolyl, etc.) tetrazolyl (e.g., 1H-tetrazolyl, 2H-tetrazolyl, etc.), etc.; unsaturated condensed heterocyclyl group containing 1 to 5 nitrogen atoms, for example, indolyl, isoindolyl, indolizinyl, benzimidazolyl, quinolyl, isoquinolyl, indazolyl, benzotriazolyl, tetrazolopyridazinyl (e.g., tetrazolo[1,5-b]pyridazinyl, etc.), etc.; unsaturated 3 to 6-membered, preferably 5- or 6-membered, heteromonocyclic group containing an oxygen atom, for example, pyranyl, furyl, etc.; unsaturated 3 to 6-membered heteromonocyclic group containing a sulfur atom, for example, thienyl, etc.; unsaturated 3 to 6-membered, preferably 5- or 6-membered, heteromonocyclic group containing 1 to 2 oxygen atoms and 1 to 3 nitrogen atoms, for example, oxazolyl, isoxazolyl, oxadiazolyl (e.g., 1,2,4-oxadiazolyl, 1,3,4-oxadiazolyl, 1,2,5-oxadiazolyl, etc.) etc.; unsaturated condensed heterocyclyl group containing 1 to 2 oxygen atoms and 1 to 3 nitrogen atoms (e.g., benzoxazolyl, benzoxadiazolyl, etc.); unsaturated 3 to 6-membered, preferably 5- or 6-membered, heteromonocyclic group containing 1 to 2 sulfur atoms and 1 to 3 nitrogen atoms, for example, thiazolyl, thiadiazolyl (e.g., 1,2,4-thiadiazolyl, 1,3,4-thiadiazolyl, 1,2,5-thiadiazolyl, etc.) etc.; unsaturated condensed heterocyclyl group containing 1 to 2 sulfur atoms and 1 to 3 nitrogen atoms (e.g., benzothiazolyl, benzothiadiazolyl, etc.) and the like.

The term "substituted" refers to the replacement of one or more hydrogen radicals in a given structure with the radical of a specified substituent including, but not limited to: halo, alkyl, alkenyl, alkynyl, aryl, heterocyclyl, thiol, alkylthio, arylthio, alkylthioalkyl, arylthioalkyl, alkyl sulfonyl, alkylsulfonylalkyl, arylsulfonylalkyl, alkoxy, aryloxy, aralkoxy, aminocarbonyl, alkylaminocarbonyl, arylaminocarbonyl, alkoxycarbonyl, aryloxycarbonyl, haloalkyl, amino, trifluoromethyl, cyano, nitro, alkylamino, arylamino, alkylaminoalkyl, arylaminoalkyl, aminoalkylamino, hydroxy, alkoxyalkyl, carboxyalkyl, alkoxycarbonylalkyl, aminocarbonylalkyl, acyl, aralkoxycarbonyl, carboxylic acid, sulfonic acid, sulfonyl, phosphonic acid, aryl, heteroaryl, heterocyclic, and aliphatic. It is understood that the substituent may be further substituted.

The term "inhibition," in the context of neoplasia, tumor growth or tumor cell growth, may be assessed by delayed appearance of primary or secondary tumors, slowed development of primary or secondary tumors, decreased occurrence of primary or secondary tumors, slowed or decreased severity of secondary effects of disease, arrested tumor growth and regression of tumors, among others. In the extreme, complete inhibition, is referred to herein as prevention or chemoprevention.

The term "metastasis," as used herein, refers to the migration of cancer cells from the original tumor site through the blood and lymph vessels to produce cancers in other tissues. Metastasis also is the term used for a secondary cancer growing at a distant site.

The term "neoplasm," as used herein, refers to an abnormal mass of tissue that results from excessive cell division. Neoplasms may be benign (not cancerous), or malignant (cancerous) and may also be called a tumor. The term "neoplasia" is the pathological process that results in tumor formation.

As used herein, the term "pre-cancerous" refers to a condition that is not malignant, but is likely to become malignant if left untreated.

The term "proliferation" refers to cells undergoing mitosis.

The term "treatment" refers to any process, action, application, therapy, or the like, wherein a mammal, including a human being, is subject to medical aid with the object of improving the mammal's condition, directly or indirectly.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describes pharmaceutically acceptable salts in detail in *J. Pharmaceutical Sciences,* 66: 1-19 (1977). The salts can be prepared in situ during the final isolation and purification of the compounds of the invention, or separately by reacting the free base function with a suitable organic acid or inorganic acid. Examples of pharmaceutically acceptable nontoxic acid addition salts include, but are not limited to, salts of an amino group formed with inorganic acids such as hydrochloric acid, hydrobromic acid, phosphoric acid, sulfuric acid and perchloric acid or with organic acids such as acetic acid, maleic acid, tartaric acid, citric acid, succinic acid lactobionic acid or malonic acid or by using other methods used in the art such as ion exchange. Other pharmaceutically acceptable salts include, but are not limited to, adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethane-sulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, picrate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, alkyl sulfonate having from 1 to 6 carbon atoms, sulfonate and aryl sulfonate. Certain salts such as the sodium, potassium and choline base salts as well as acidic salts such as sulfate and methanesulfonate salts have been found to improve the solubility of compounds of Formula I in pharmaceutically acceptable aqueous media. In one embodiment, the pharmaceutically acceptable salt of Compound 1 is the choline salt. Preferred salts of Compound 1 include the sodium salt and the potassium salt. Other preferred salts include the sulfate and methanesulfonate salts. Particularly preferred salts of Compound 1 are the methanesulfonate and benzenesulfonate salts. A particularly preferred salt of Compound 2 is the hydrochloride salt.

As used herein, "pharmaceutically acceptable carrier" is intended to include any and all solvents, dispersion media, coatings, antibacterial and antifungal agents, isotonic and absorption delaying agents, and the like, compatible with pharmaceutical administration, such as sterile pyrogen-free water. Suitable carriers are described in the most recent edition of Remington's Pharmaceutical Sciences, a standard reference text in the field, which is incorporated herein by reference. Preferred examples of such carriers or diluents include, but are not limited to, water, saline, Ringer's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

As used herein, the term "pre-cancerous" refers to a condition that is not malignant, but is likely to become malignant if left untreated.

The term "subject" as used herein refers to an animal. Preferably the animal is a mammal. More preferably the mammal is a human. A subject also refers to, for example, dogs, cats, horses, cows, pigs, guinea pigs, fish, birds and the like.

The compounds of this invention may be modified by appending appropriate functionalities to enhance selective biological properties. Such modifications are known in the art and may include those which increase biological penetration into a given biological system (e.g., blood, lymphatic system, central nervous system), increase oral availability, increase solubility to allow administration by injection, alter metabolism and alter rate of excretion.

Pharmaceutical Compositions

The pharmaceutical compositions of the present invention comprise a therapeutically effective amount of a compound of Formula I, such as Compound 1, or a pharmaceutically acceptable salt thereof in combination with a PD-1 signaling inhibitor, formulated together with one or more pharmaceutically acceptable carriers or excipients.

Preferably, the pharmaceutically acceptable carrier or excipient is a non-toxic, inert solid, semi-solid or liquid filler, diluent, encapsulating material or formulation auxiliary of any type. Some examples of materials which can serve as pharmaceutically acceptable carriers are sugars such as lactose, glucose and sucrose; cyclodextrins such as alpha- ($\alpha$), beta- ($\beta$) and gamma- ($\gamma$) cyclodextrins; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil, safflower oil, sesame oil, olive oil, corn oil and soybean oil; glycols such as propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator.

The pharmaceutical compositions of this invention may be administered orally, parenterally, by inhalation spray, topically, rectally, nasally, buccally, vaginally or via an implanted reservoir, preferably by oral administration or administration by injection. The pharmaceutical compositions of this invention may contain any conventional non-toxic pharmaceutically-acceptable carriers, adjuvants or vehicles. In some cases, the pH of the formulation may be adjusted with pharmaceutically acceptable acids, bases or buffers to enhance the stability of the formulated compound or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose, any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution, which, in turn, may depend upon crystal size and crystalline form. Alternatively, delayed absorption of a parenterally administered drug form is accomplished by dissolving or suspending the drug in an oil vehicle. Injectable depot forms are made by forming microencapsule matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides). Depot injectable formulations are also prepared by entrapping the drug in liposomes or microemulsions that are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or: a) fillers or extenders such as starches, lactose, sucrose, glucose, mannitol, and silicic acid; b) binders such as, for example, carboxymethylcellulose, alginates, gelatin, polyvinylpyrrolidinone, sucrose, and acacia; c) humectants such as glycerol; d) disintegrating agents such as agar-agar, calcium carbonate, potato or tapioca starch, alginic acid, certain silicates, and sodium carbonate; e) solution retarding agents such as paraffin; f) absorption accelerators such as quaternary ammonium compounds; g) wetting agents such as, for example, cetyl alcohol and glycerol monostearate; h) absorbents such as kaolin and bentonite clay; and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

For pulmonary delivery, a therapeutic composition of the invention is formulated and administered to the patient in solid or liquid particulate form by direct administration (e.g., inhalation into the respiratory system). Solid or liquid particulate forms of the active compound prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. No. 5,767,068 to Van Devanter et al., U.S. Pat. No. 5,508,269 to Smith et al., and WO 98/43650 by Montgomery, all of which are incorporated herein by reference). A discussion of pulmonary delivery of antibiotics is also found in U.S. Pat. No. 6,014,969, incorporated herein by reference.

By a "therapeutically effective amount" of a combination of the compound of Formula I and the PD-1 signaling inhibitor is meant an amount of each compound which in combination confers a therapeutic effect on the treated subject, at a reasonable benefit/risk ratio applicable to any medical treatment. The therapeutic effect may be objective (i.e., measurable by some test or marker) or subjective (i.e., subject gives an indication of or feels an effect). Effective doses will also vary depending on route of administration, as well as the possibility of co-usage with other agents. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or contemporaneously with the specific compound employed; and like factors well known in the medical arts. In preferred embodiments, the therapeutically effective amount of the combination of the compound of Formula I or pharmaceutically acceptable salt thereof and the PD-1 signaling inhibitor, exhibits synergism in the cancer type to be treated.

The total daily dose of each compound in the combination therapy of this invention administered to a human or other animal in single or in divided doses can be in amounts, for example, from 0.01 to 50 mg/kg body weight or more usually from 0.1 to 25 mg/kg body weight. Single dose compositions may contain such amounts or submultiples thereof to make up the daily dose. In general, treatment regimens according to the present invention comprise administration to a patient in need of such treatment from about 10 mg to about 1000 mg of the compound(s) of this invention per day in single or multiple doses.

Each compound in the combination therapy of the invention can, for example, be administered by injection, intravenously, intraarterially, subdermally, intraperitoneally, intramuscularly, or subcutaneously; or orally, buccally, nasally, transmucosally, topically, in an ophthalmic preparation, or by inhalation, with a dosage ranging from about 0.1 to about 500 mg/kg of body weight, alternatively dosages between 1 mg and 1000 mg/dose, every 4 to 120 hours, or according to the requirements of the particular drug. The methods herein contemplate administration of an effective amount of compound or compound composition to achieve the desired or stated effect. Typically, the pharmaceutical compositions of this invention will be administered from about 1 to about 6 times per day or alternatively, as a continuous infusion. Such administration can be used as a chronic or acute therapy. The amount of active ingredient that may be combined with pharmaceutically excipients or carriers to produce a single dosage form will vary depending upon the host treated and the particular mode of administration. A typical preparation will contain from about 5% to about 95% active compound (w/w). Alternatively, such preparations may contain from about 20% to about 80% active compound.

Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Upon improvement of a patient's condition, a maintenance dose of a compound, composition or combination of this invention may be administered, if necessary. Subsequently, the dosage or frequency of administration, or both, may be reduced, as a function of the symptoms, to a level at which the improved condition is retained when the symptoms have been alleviated to the desired level. Patients may, however, require intermittent treatment on a long-term basis upon any recurrence of disease symptoms.

EXAMPLES

The compounds and processes of the present invention will be better understood in connection with the following examples, which are intended as an illustration only and not limiting of the scope of the invention. Various changes and modifications to the disclosed embodiments will be apparent to those skilled in the art and such changes and modifications including, without limitation, those relating to the chemical structures, substituents, derivatives, formulations and/or methods of the invention may be made without departing from the spirit of the invention and the scope of the appended claims.

The synthesis of Compound 1 and the methanesulfonate, sodium, potassium and choline salts thereof is illustrated in the schemes below.

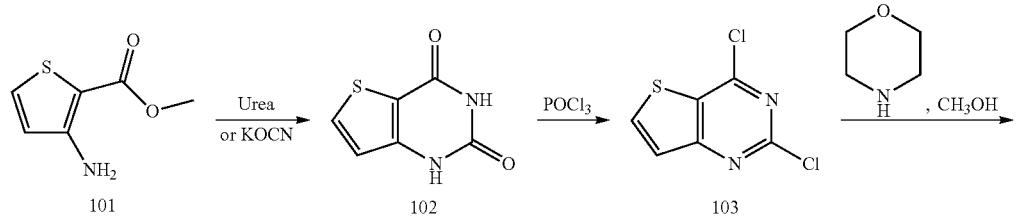

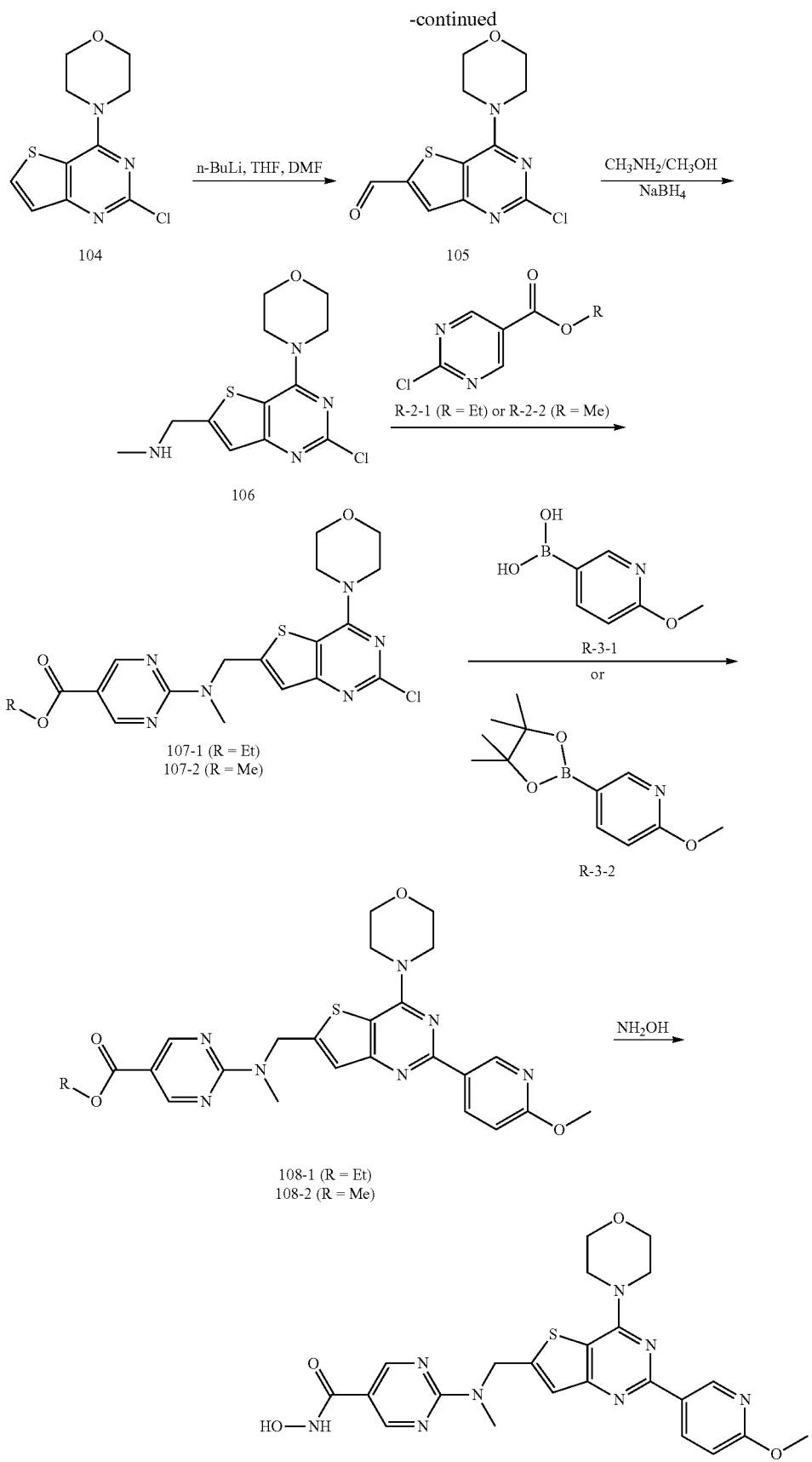

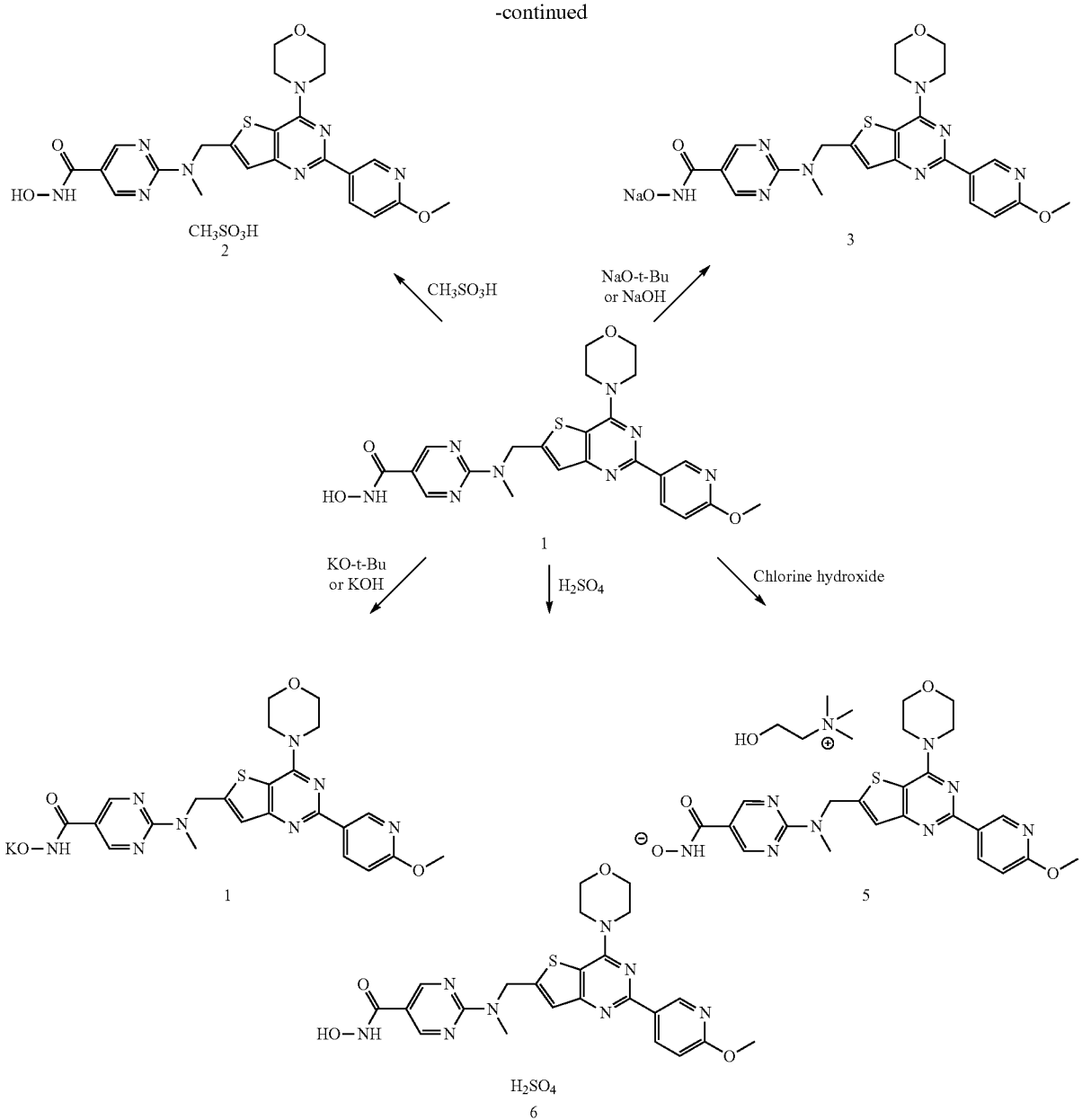
The intermediate 107-1 or 107-2 can be prepared by reacting 106 with either R-2-1 or R-2-2, respectively. The synthetic schemes for the synthesis of R-2-1 and R-2-2 are illustrated below:
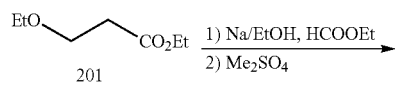
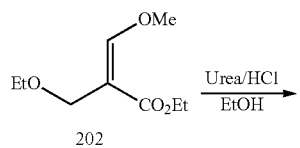
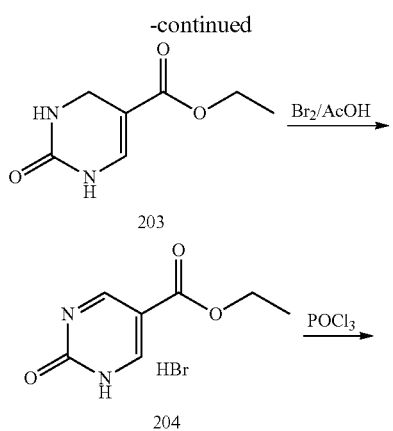

-continued
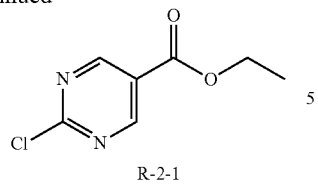
Or by an alternative method:
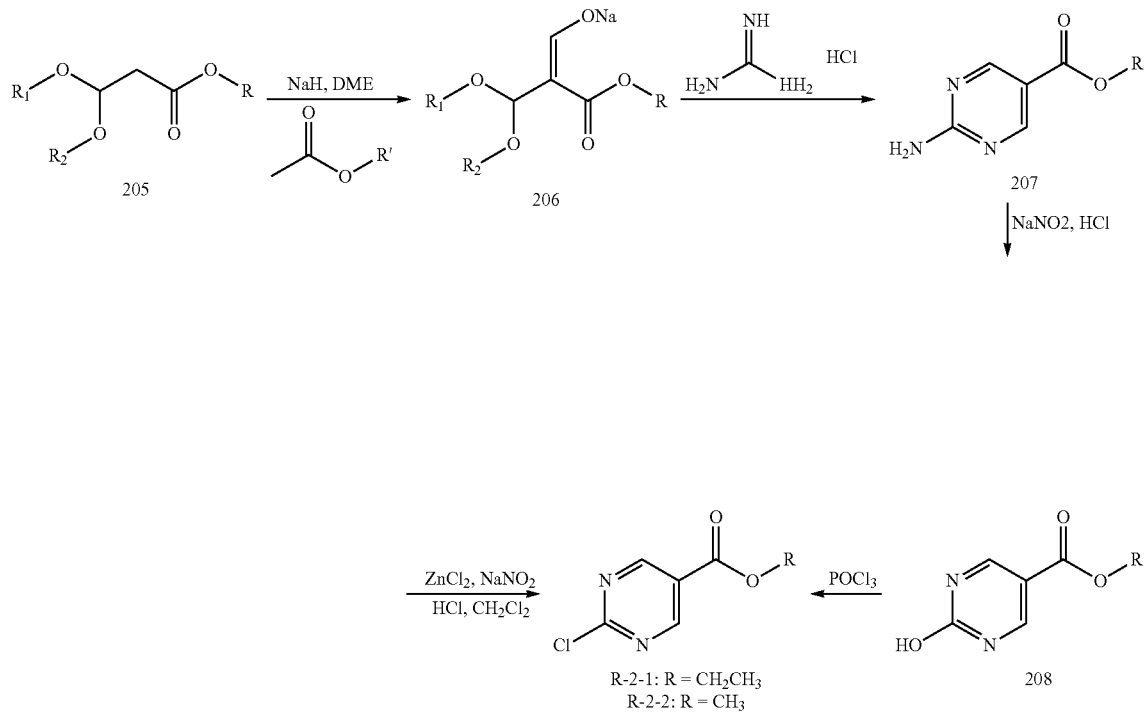
Intermediate 108-1 and 108-2 can be prepared by the coupling reaction of 107-1 or 107-2 with either R-3-1 or R-3-2, where R-3-1 and R-3-2 can be prepared according to the following scheme:
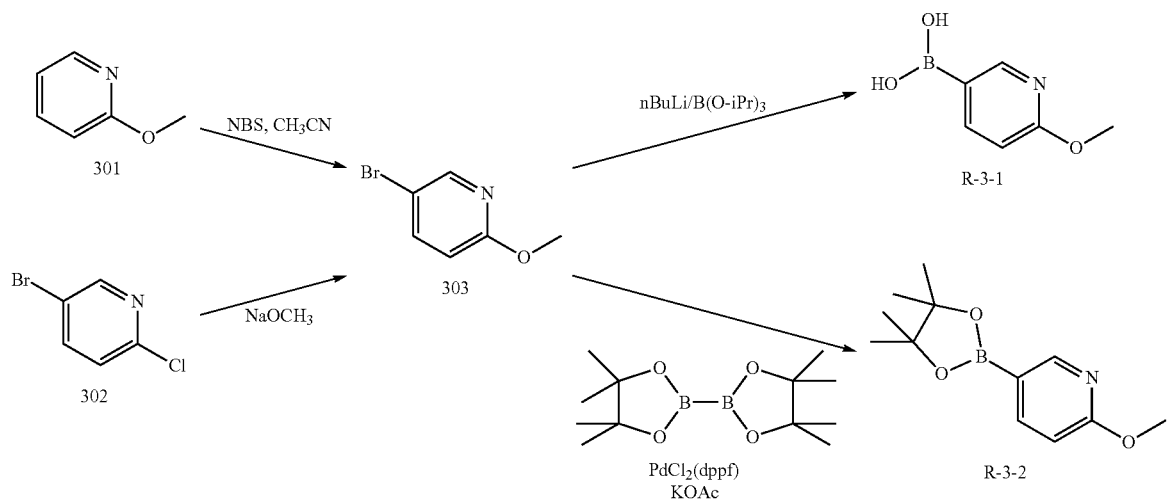

Example 1: Preparation of N-hydroxy-2-0(2-(6-methoxypyridin-3-yl)-4-morpholinothieno[3,2-d]pyrimidin-6-yl)methyl)(methyl)amino)pyrimidine-5-carboxamide (Compound 1)

Step a: (Z)-Ethyl-2-(ethoxymethyl)-3-methoxyacrylate (Compound 202)

Sodium (40.9 g, 1.78 mol) was added to ethanol (750 mL) in portions carefully and the solution was concentrated to give NaOEt powder after all sodium metal disappeared. Under stirring, hexane (1.0 L) was added and the mixture was cooled with ice-water bath. A mixture of 201 (130 g, 0.89 mol) and ethyl formate (131 g, 1.78 mol) was added dropwise at 0-5° C. The reaction mixture was stirred at room temperature overnight. Dimethyl sulfate (224 g, 1.78 mol) was added dropwise with cooling of ice-water bath. The resulting mixture was heated at 50° C. for 2 h. To the mixture was added triethylammonium chloride (122 g) and sodium hydroxide (20 g). The mixture was then stirred at room temperature for 4 h and filtered. The filtrate was washed with water and dried over $Na_2SO_4$. It was concentrated to afford the titled compound (140 g, 37%) as a colorless oil which was used in the next step without further purification.

Step b: Ethyl 2-oxo-1,2,3,4-tetrahydropyrimidine-5-carboxylate (Compound 203)

A mixture of compound 202 (140 g, 0.745 mol), urea (40.0 g, 0.697 mol) and concentrated hydrochloric acid (34 mL) in ethanol (500 mL) was heated at reflux overnight. After evaporating ~50% of volume of reaction, the resulting suspension was filtered, washed with small amount of ethanol, and dried to give compound 203 (47 g, 37%) as a white solid. LCMS: 171 $[M+1]^+$. $^1$H NMR (400 MHz, $CDCl_3$): δ 1.19 (t, J=7.2 Hz, 3H), 3.92 (s, 2H), 4.08 (q, J=7.2 Hz, 2H), 7.0 (s, 1H), 7.08 (d, J=6.0 Hz, 1H), 8.83 (d, br, J=4.8 Hz, 1H).

Step c: Ethyl 2-oxo-1,2-dihydropyrimidine-5-carboxylate (Compound 204)

To a solution of compound 203 (47 g, 280 mmol) in acetic acid (500 mL) was added bromine (49.0 g, 307 mmol). The mixture was heated at reflux for 2 h, cooled to room temperature, further cooled at 0-5° C. and filtered to give the title compound 204 as a yellow solid (38 g, 54%). LCMS: 169 $[M+1]^+$. $^1$H NMR (400 MHz, $D_2O$): δ 1.28 (t, J=7.2 Hz, 3H), 4.32 (q, J=7.2 Hz, 2H), 9.00 (br, s, 2H).

Step d: Ethyl 2-chloropyrimidine-5-carboxylate (Compound R-2-1)

A mixture of compound 204 (38.0 g, 153 mmol) and phosphoryl trichloride (300 mL) and N,N-dimethylaniline (3 mL) was heated at reflux for 2 h, cooled to room temperature and concentrated. The residue was quenched carefully with ice-water, adjusted pH to 7-8 with sodium carbonate and extracted with EtOAc. The combined organics were washed with ice-water and brine, dried over $Na_2SO_4$, evaporated, and purified by column chromatography (eluted with EtOAc/Hexanes, 10%) to afford compound R-2-1 (15 g, 52%) as a white solid. LCMS: 187 $[M+1]^+$. $^1$H NMR (400 MHz, $CDCl_3$): δ 1.36 (t, J=7.5 Hz, 3H), 4.39 (q, J=7.5 Hz, 2H), 9.08 (s, 2H).

Step e: Sodium (Z)-2-(dimethoxymethyl)-3-methoxy-3-oxoprop-1-en-1-olate (Compound 206)

A mixture of NaH (27 g, 60% in mineral oil, 0.675 mol) in anhydrous 1,2-dimethoxyethane (300 mL) was heated to 40-50° C. and methyl 3,3-dimethoxy propionate (205) (100 g, 0.675 mol) was added dropwise. The resulting mixture was stirred for 0.5 h and anhydrous methyl formate (81 g, 1.35 mol) was added dropwise at 40-50° C. The resulting mixture was stirred at 40-50° C. (inner temperature) for 2 h before it was cooled to 0° C. The reaction mixture was allowed to warm to 25° C. slowly and stirred overnight. $Et_2O$ (150 mL) was added and stirred for 30 min. The resulting suspension was filtered. The solid was washed with $Et_2O$ (100 mL), collected and dried to afford the title compound 206 (82 g, 61%) as an off-white solid. LCMS (m/z): 130.8 $[M+1]^+$. $^1$H NMR (400 MHz, $CD_3OD$): δ 3.36 (s, 6H), 3.60 (s, 3H), 5.34 (s, 1H), 8.92 (s, 1H).

Step f: 2-Amino-pyrimidine-5-carboxylic acid methyl ester (Compound 207)

To a mixture of guanidine hydrochloride (42.2 g, 0.44 mol) in DMF (300 mL) was added compound 206 (80 g, 0.40 mol). The resulting mixture was heated at 100° C. for 1 h. The reaction mixture was filtered before cooled. The filter cake was washed with 50 mL of DMF and the combined filtrate was concentrated to leave a residue which was suspended in cold EtOH and washed with cold EtOH (50 mL) to afford the compound 207 (38 g, 61.5%) as a yellow solid. LCMS (m/z): 154.2 $[M+1]^+$, 195.1$[M+42]^+$. $^1$H NMR (400 MHz, $CD_3OD$): δ 3.88 (s, 3H), 8.77 (s, 2H).

Step g: Methyl 2-chloropyrimidine-5-carboxylate (Compound R-2-2)

Compound 207 (7 g, 0.046 mol) was added to a mixture of concentrated hydrochloric acid (15.2 mL) and $CH_2Cl_2$ (60 mL). After cooling, $ZnCl_2$ (18.6 g, 0.138 mol) was added at 15-20° C. The mixture was stirred at 15-20° C. for 0.5 h and cooled to 5-10° C. $NaNO_2$ (9.5 g, 0.138 mol) was added portion wise while keeping the internal temperature 5-10° C. The reaction was continued for ~2 h. The reaction mixture was poured into ice-water (50 mL). The organic layer was separated and the aqueous phase was extracted with $CH_2Cl_2$ (30 mL*2). The combined organic extracts were concentrated to afford crude product (4.2 g). The crude compound was suspended in hexane (20 mL), heated at 60° C. for 30 minutes and filtered. The filtrate was concentrated to afford the title compound R-2-2 (3.5 g, 44.4%) as an off-white solid. LCMS (m/z): 214.1$[M+42]^+$. $^1$H NMR (400 MHz, $CDCl_3$): δ 4.00 (s, 3H), 9.15 (s, 2H).

Step h: 5-Bromo-2-methoxypyridine (Compound 303)

A solution of 2-methoxy-pyridine (100 g, 0.92 mole), NBS (180 g, 1.0 mole) in acetonitrile (1.0 L) was stirred at reflux for 21 h. TLC showed that the reaction was complete. The reaction mixture was cooled to room temperature and concentrated. ~900 ml solvent was collected. The resulting suspension was filtered and washed with n-hexane (~400 mL). The filtrate was concentrated again to afford crude product. The crude product was distilled at reduced pressure (30° C./~0.3 mmHg) to afford the title compound as a clear oil (146 g, 84%). LCMS (m/z): 190.0 $[M+1]^+$. $^1$H NMR (400

MHz, CDCl$_3$): δ 3.90 (s, 3H), 6.65 (d, J=8.8 Hz, 1H), 7.62 (dd, J=8.8 Hz, 2.4 Hz, 1H), 8.19 (s, 1H).

Step i: 6-Methoxypyridin-3-ylboronic Acid (R-3-1)

To a solution of compound 303 (20 g, 0.11 mole) in anhydrous THF (180 ml) was added dropwise n-BuLi (59 mL, 2M in THF) at −78° C., the resulting mixture was stirred for 1 h. Triisopropyl borate (37 mL) was added at −78° C. and the reaction mixture was warmed to room temperature and continued to stir overnight. TLC (hexanes/ethyl acetate=5:1) showed reaction complete. The mixture was adjusted pH to 3-4 with 4N HCl (90 ml). The precipitate was collected by filtration to afford crude compound R-3-1 (21 g, 128%). The crude compound R-3-1 (21 g) was dissolved in water (200 ml) and the solution was adjusted pH to 8-9 with concentrated ammonia solution, the precipitate was collected by filtration to afford the pure title compound R-3-1 as a white solid. (11 g, 67%). LCMS (m/z): 154.1 [M+1]$^+$. $^1$H NMR (400 MHz, DMSO-d$_6$): δ 3.86 (s, 3H), 6.76 (d, J=8.4 Hz, 1H), 7.99 (dd, J=8.4 Hz, 2.0 Hz, 1H), 8.05 (br, 2H), 8.52 (d, J=2.0 Hz, 1H).

Step j: 2-methoxy-5-(4,4,5,5-tetramethyl-1,3,2-dioxaborolan-2-yl)pyridine (Compound R-3-2)

A mixture of compound 303 (55 g, 0.29 mol), 4,4,4',4',5,5,5',5'-octamethyl-2,2'-bi(1,3,2-dioxaborolane) (90 g, 0.35 mol), potassium acetate (57 g, 0.58 mol) and bis(triphenylphosphine)palladium(II) chloride (2.2 g, 3 mmol) in anhydrous dioxane (500 mL) was heated at 108° C. under N$_2$ atmosphere overnight. The reaction mixture was concentrated and purified by column chromatography eluted with hexanes/ethyl acetate to afford title compound R-3-2 (58 g, 84%). $^1$H NMR (400 MHz, DMSO-d$_6$): δ 1.30 (s, 12H), 3.88 (s, 3H), 6.81 (d, J=8.0 Hz, 1H), 7.88 (dd, J=8.0 Hz, 2.0 Hz, 1H), 8.41 (d, J=2.0 Hz, 1H).

Step k: Thieno[3,2-d]pyrimidine-2,4(1H,3H)-dione (Compound 102)

Urea Method:
A mixture of methyl 3-aminothiophene-2-carboxylate (101) (90.0 g, 573 mmol, 1.0 eq) and urea (277.6 g, 4.6 mol, 8.0 eq) was heated at 190° C. for 3-4 h and cooled to room temperature. To the reaction mixture was added aq. NaOH (10%, 800 mL). After stirring at ambient temperature for 1 h, the solid was removed by filtration. The filtrate was acidified with HCl to pH 3-4, the precipitated solid was collected by filtration, washed with water and dried in vacuo to give the desired product compound 102 as an off-white solid (87 g, 89%). m.p.: 280-285° C. LCMS (m/z): 169.0 [M+1]$^+$. $^1$H NMR (400 MHz, DMSO-d$_6$): δ 6.92 (d, J=5.2 Hz, 1H), 8.05 (d, J=5.2 Hz, 1H), 11.0-11.5 (br, 2H).

KOCN Method:
To a mixture of 3-aminothiophene-2-carboxylate (101) (100.0 g, 636.9 mmol, 1.0 eq), acetic acid (705 mL) and water (600 mL) was added a solution of potassium cyanate (154.8 g, 1.91 mol, 3.0 eq) in water (326 mL) slowly over a period of 1 h. The resulting mixture was stirred at room temperature for 20 h, filtered and rinsed with water (500 mL). The cake was charged to a suitably sized reactor and 2 M aqueous sodium hydroxide solution (1.65 L) was added, the slurry was stirred for 2 h and LCMS confirmed the formation of the desired product. The mixture was cooled to 10° C. and 3 M aqueous hydrochloric acid (1.29 L) was added until the pH=5.0-6.0. The slurry was filtered, rinsed with water (700 mL), and dried in vacuum oven at 50° C. for 24 h to afford compound 102 (100 g, 94%) as an off-white solid. LCMS (m/z): 169.1 [M+1]$^+$. $^1$H NMR (400 MHz, DMSO-d$_6$): δ 6.92 (d, J=5.2 Hz, 1H), 8.04 (d, J=5.2 Hz, 1H), 11.14 (s, 1H), 11.51 (s, 1H).

Step 1: 2,4-Dichlorothieno[3,2-d]pyrimidine (Compound 103)

Phosphorous oxychloride (152 mL, 1.67 mol, 7.0 eq) was added slowly to cold solution of compound 102 (40 g, 238 mmol, 1.0 eq) and N,N-dimethylaniline (22.5 mL, 179 mmol, 0.75 eq) in acetonitrile (250 mL) while maintaining the temperature below 20° C. The mixture was then heated to 85° C. and stirred for 24 h. The reaction mixture was cooled to 15° C., and then poured slowly onto a mixture of ice and cold water (360 mL). The resulting slurry was filtered, rinsed with cold water (200 mL). The cake was dried in vacuum oven at 40° C. for 24 h to afford compound 103 (40.5 g, 83%) as an off-white solid. M.p.: 245-250° C. LCMS (m/z): 205.0 [M+1]$^+$. $^1$H NMR (400 MHz, DMSO-d$_6$): δ 7.75 (d, J=5.2 Hz, 1H), 8.71 (d, J=5.2 Hz, 1H).

Step m: 2-Chloro-4-morpholinothieno[3,2-d]pyrimidine (Compound 104)

To a mixture of compound 103 (34.2 g, 167 mmol, 1.0 eq) and methanol (500 mL) was added morpholine (31.2 mL, 367 mmol, 2.2 eq) slowly. The reaction mixture was stirred at room temperature overnight. The precipitate was collected by filtration, washed with methanol and dried in vacuo to give the desired product compound 104 as a light-yellow solid (39 g, 91%). M.p.: 250-255° C. LCMS (m/z): 256.0 [M+1]$^+$. $^1$H NMR (400 MHz, DMSO-d$_6$): δ 3.76 (t, J=5.2 Hz, 4H), 3.92 (t, J=5.2 Hz, 4H), 7.42 (d, J=5.2 Hz, 1H), 8.32 (d, J=5.2 Hz, 1H).

Step n: 2-Chloro-4-morpholinothieno[3,2-d]pyrimidine-6-carbaldehyde (Compound 105)

To a suspension of compound 104 (20 g, 78.4 mmol, 1.0 eq) in THF (anhydrous, 320 mL) at −78° C. was added n-BuLi (in hexanes, 2.4 M, 40.8 mL, 102 mmol, 1.3 eq) slowly under nitrogen. The resulting slurry was allowed to warm up to −60° C. to turn into a clear brown solution. The reaction mixture was then cooled to −78° C. again and DMF (anhydrous, 9.1 mL, 118 mmol, 1.5 eq) was added slowly. The resulting solution was stirred at −78° C. for 0.5 h, warmed up to 0° C. over 1 h and was poured slowly to a mixture of aq HCl (0.25 M, 660 mL) and ice water (320 mL). The resulting slurry was stirred at 0-10° C. for 0.5 h, filtered, washed with cold water and dried in vacuo to afford compound 105 as a yellow solid (22 g, 98%). M.p.: 260-265° C. LCMS (m/z): 284.0 [M+1]$^+$ $^1$H NMR (400 MHz, DMSO-d$_6$): δ 3.77 (t, J=5.2 Hz, 4H), 3.96 (t, J=5.2 Hz, 4H), 8.30 (s, 1H), 10.21 (s, 1H).

Step o: (2-Chloro-4-morpholin-4-yl-thieno[3,2-d]pyrimidin-6-ylmethyl)-methyl-amine (Compound 106)

To a solution of compound 105 (20.0 g, 70.4 mmol, 1.0 eq) in methanol (125 mL) was added methylamine solution in methanol (27% v/v, 75 mL, 563.2 mmol) under nitrogen atmosphere. The reaction mixture was stirred at room temperature overnight and the solvent was removed in vacuo to give a crude solid product, which was dissolved in methanol (550 mL) and THF (220 mL) under nitrogen. Sodium borohydride (8 g, 211.2 mmol) was added in portions and reaction mixture was stirred at room temperature overnight. The reaction mixture was evaporated in vacuo and water (300 mL) was added. The aqueous mixture was extracted with methylene chloride and the combined extracts were dried over $Na_2SO_4$ and concentrated. The residue was dissolved in 6M HCl (230 mL) and stirred for 30 min. The aqueous solution was washed with methylene chloride for several times, and adjusted to pH 9-10 with NaOH (4N). The precipitated solid was collected by filtration and dried (60° C., 6 h) to give a light yellow solid (18 g, 85%). M.p.: 240-245° C. LCMS (m/z): 299 [M+1]$^+$. $^1$H NMR (400 MHz, DMSO-$d_6$): δ 2.32 (s, 3H), 3.74 (t, J=5.2 Hz, 4H), 3.88 (t, J=5.2 Hz, 4H), 3.96 (s, 2H), 7.24 (s, 1H).

Step p(a): 2-[(2-Chloro-4-morpholin-4-yl-thieno[3,2-d]pyrimidin-6-ylmethyl)-methyl-amino]-pyrimidine-5-carboxylic Acid Ethyl Ester (Compound 107-1)

To a mixture of 106 (10 g, 33.6 mmol) and R-2-1 (6.8 g, 36.4 mmol) in $CH_3CN$ (400 mL) at room temperature was added diisopropylethylamine (220 mL, 1.26 mol). The resulting mixture was stirred at room temperature overnight. The mixture was then evaporated and followed by the addition of methylene chloride (300 mL). The organic phase was washed with water, dried over $Na_2SO_4$ and concentrated in vacuo to leave a residue. To the residue was added ethyl acetate and the resulting mixture was stirred at ice/water bath temperature for 50 min. The resulting solid was collected by filtration to give the titled product 107-1 as a white solid (10.6 g, 70%). LCMS: 449 [M+1]$^+$. $^1$H NMR (400 MHz, DMSO-$d_6$): δ 1.30 (t, J=7.2 Hz, 3H), 3.25 (s, 3H), 3.71 (t, J=5.2 Hz, 4H), 3.83 (t, J=4.8 Hz, 4H), 4.29 (m, 2H), 5.21 (s, 2H), 7.39 (s, 1H), 8.87 (s, 2H).

Step p(b): 2-[(2-Chloro-4-morpholin-4-yl-thieno[3,2-d]pyrimidin-6-ylmethyl)-methyl-amino]-pyrimidine-5-carboxylic Acid Methyl Ester (Compound 107-2)

A mixture of compound 106 (25 g, 84 mmol), $CH_3CN$ (500 mL) and R-2-2 (16 g, 92 mmol) was stirred at room temperature. Diisopropylethylamine (DIPEA) (500 mL, 2.9 mol) was added. The solution was stirred overnight and evaporated. After methylene chloride (500 mL) was added, the organic phase was washed with water, dried with $Na_2SO_4$ and concentrated in vacuo. To the residue was added ethyl acetate (200 mL) and the mixture was stirred in ice/water bath for 50 min. The title product was collected as a white solid (29.4 g, 81%). LCMS (m/z): 435.2 [M+1]$^+$. $^1$H NMR (400 MHz, DMSO-$d_6$): 3.25 (s, 3H), 3.71 (t, J=5.2 Hz, 4H), 3.82-3.84 (m, 7H), 5.21 (s, 2H), 7.39 (s, 1H), 8.87 (s, 2H).

Step q(a): Ethyl-2-(((2-(6-methoxypyridin-3-yl)-4-morpholinothieno[3,2-d]pyrimidin-6-yl)methyl)(methyl)amino)pyrimidine-5-carboxylate (Compound 108-1)

Method A: A mixture of compound 107-1 (12 g, 26.7 mmol), R-3-1 (4.9 g, 32 mmol), $NaHCO_3$ (6.7 g, 80.1 mmol) and bis(triphenylphosphine)palladium(II) chloride (188 mg, 0.267 mmol) in a mixed solvents of toluene (80 ml), ethanol (50 ml) and water (10 ml) was heated at 108° C. for 4.5 h under $N_2$ atmosphere. TLC showed reaction was complete. The reaction mixture was then cooled to room temperature and water (20 ml) was added. The resulting solid was collected by filtration and was then suspended in ethanol (100 mL). The suspension was stirred at room temperature for 30 minutes and filtered. The collected solid was washed with ethanol and dried in vacuo to afford titled compound 108-1 as a white solid (10 g, 72%).

Method B: A mixture of compound 107-1 (1.5 g, 3.34 mmol), R-3-2 (1.6 g, 6.68 mmol), $NaHCO_3$ (0.84 g, 10.0 mmol) and bis(triphenylphosphine)palladium(II) chloride (118 mg, 0.167 mmol) in a mixed solvents of toluene (24 ml), ethanol (15 ml), and water (3 ml) was heated at 108° C. under $N_2$ atmosphere overnight. The reaction mixture was partitioned between dichloromethane and water. The organic layer was separated and was washed with brine, dried over $Na_2SO_4$, filtered and evaporated in vacuo to give a residue which was purified by column chromatography eluted with hexanes/ethyl acetate to afford compound 108-1 as a white solid (1.7 g, 98%).

m.p. 198-202° C. LCMS: 522.30 [M+1]$^+$. $^1$H NMR (400 MHz, DMSO-$d_6$): δ 1.31 (t, J=7.2 Hz, 3H), 3.28 (s, 3H), 3.76 (t, J=4.4 Hz, 4H), 3.93 (t, J=4.4 Hz, 4H), 3.94 (s, 3H), 4.30 (q, J=7.2 Hz, 2H), 5.24 (s, 2H), 6.92 (d, J=8.8 Hz, 1H), 7.47 (s, 1H), 8.57 (dd, J=8.8 Hz, 2.0 Hz, 1H), 8.88 (s, 2H), 9.15 (d, J=2.0 Hz, 1H).

Step q(b): Methyl-2-(((2-(6-methoxypyridin-3-yl)-4-morpholinothieno[3,2-d]pyrimidin-6-yl)methyl)(methyl)amino)pyrimidine-5-carboxylate (Compound 108-2)

To a mixture of compound 107-2 (20 g, 46.0 mmol), B-3-1 (9.2 g, 60.2 mmol, 1.3 eq.) in dioxane (540 mL) at room temperature was added solid $NaHCO_3$ (11.6 g, 138.1 mmol, 3 eq.) followed by the addition of water (40 mL). The resulting mixture was degassed by passing $N_2$ through surface of solution. Bis(triphenylphosphine) palladium(II) chloride (323 mg, 0.46 mmol, 0.01 eq.) was then added and the resulting mixture was heated at 108° C. for 15 h. TLC and LCMS showed reaction complete. The reaction mixture was filtered through Celite while it was still hot (>90° C.) and washed with dioxane (70 mL). The filtrate was cooled gradually to room temperature and white fine crystals formed during cooling period. The suspension was filtered and washed with dioxane (80 mL) to afford the titled compound 108-2 as a white solid (18 g, 78%). LCMS (m/z): 508.3 [M+1]$^+$. $^1$H NMR (400 MHz, DMSO-$d_6$): δ 3.28 (s, 3H), 3.76 (t, J=4.8 Hz, 4H), 3.82 (s, 3H); 3.92 (m, 4H), 3.93 (s, 3H), 5.20 (s, 2H), 6.91 (d, J=8.8 Hz, 1H), 7.47 (s, 1H), 8.57 (dd, J=8.8 Hz, 2.4 Hz, 1H), 8.88 (s, 2H), 9.15 (d, J=2.0 Hz, 1H).

Step r: N-Hydroxy-2-(((2-(6-methoxypyridin-3-yl)-4-morpholinothieno[3,2-d]pyrimidin-6-yl)methyl)(methyl)amino)pyrimidine-5-carboxamide (Compound 1)

Preparation of Hydroxylamine Methanol Solution

A mixture of $NH_2OH \cdot HCl$ (80 g, 1.12 mol) in MeOH (400 mL) was heated at 60-65° C. for 1 h to form a clear solution. It was then cooled in an ice-water bath. To the cold mixture was added a solution of KOH (96 g, 1.68 mol) in MeOH (240 mL) dropwise while maintaining the reaction temperature at 0-10° C. The resulting mixture was stirred at 0° C. for 30 minutes and then filtered through a constant pressure funnel filled with anhydrous $Na_2SO_4$ (700 g). The filtrate was collected under an ice-bath and stored in refrigerator for future use.

Preparation of Compound 1 from Compound 108-1

Compound 108-1 (10 g, 19 mmol) was suspended in the above freshly prepared hydroxylamine methanol solution (1.79M, 350 ml). To this mixture was added dichloromethane (100 mL). The reaction flask was sealed and the mixture was stirred at room temperature for 5 h before it turned into clear solution. Reaction was stirred for additional 9 h. and was filtered to remove any insoluble solid. The filtrate was adjusted to pH 6-7 with the addition of acetic acid to form solid precipitate. The solid was collected by filtration and washed with water and minimum amount of methanol, dried in vacuo at 60° C. for 5 h to afford compound 1 as a white solid (9.2 g, 96%). m.p. 177-180° C. LCMS: 509.3 [M+1]$^+$. $^1$H NMR (400 MHz, DMSO-$d_6$): δ 3.24 (s, 3H), 3.76 (t, J=5 Hz, 4H), 3.92 (t, J=5 Hz, 4H), 3.92 (s, 3H), 5.20 (s, 2H), 6.90 (d, J=8.8 Hz, 1H), 7.44 (s, 1H), 8.57 (dd, J=8.8 Hz, 2.4 Hz, 1H), 8.75 (s, 2H), 9.01 (s, 1H), 9.14 (d, J=2.0 Hz, 1H), 11.08 (s, 1H).

Preparation of Compound 1 from Compound 108-2

To a suspension of compound 108-2 (31 g, 61.1 mmol) in dichloromethane (310 mL) at room temperature was added above freshly prepared hydroxylamine methanol solution (1.79M, 744 ml). The reaction flask was sealed and the reaction mixture was stirred at room temperature for 5 h. The reaction mixture turned into a clear solution. The reaction solution was filtered to remove any insoluble solid. To the filtrate was then added water (310 mL) and there was no solid formed during the addition. Acetic acid (18.5 mL) was added to adjust pH to 10.20 (continuously monitored by pH meter) while stirring. There was no internal temperature change during acetic acid addition. The resulting reaction mixture was continued to stir for another 4 h. White solid gradually formed. The suspension was filtered and washed with minimum amount of methanol (100 mL×3). The collected white solid was re-suspended in methanol (620 mL) and water (124 mL) to form a suspension. To the above suspension was added additional acetic acid (11 g) to adjust the pH to 5-6. The change of the solid form was observed. The suspension was continued to stir for another 2 h and filtered through filter paper and washed with minimum amount of methanol (100 mL×3). The collected white solid was dried in oven (50° C.) for 12 h to afford the title Compound 1 as a white solid (23.6 g, 76.0%). m. p.: 255-259° C. LCMS (m/z): 509.3 [M+1]$^+$. $^1$H NMR (400 MHz, DMSO-$d_6$): δ 3.24 (s, 3H), 3.76 (t, J=5.2 Hz, 4H), 3.92 (t, J=5.2 Hz, 4H), 3.92 (s, 3H), 5.20 (s, 2H), 6.91 (d, J=8.4 Hz, 1H), 7.45 (s, 1H), 8.57 (dd, J=8.4 Hz, 2.4 Hz, 1H), 8.75 (s, 2H), 9.07 (s, 1H), 9.14 (d, J=2.4 Hz, 1H), 11.14 (s, 1H).

Example 2: Preparation of N-hydroxy-2-(((2-(6-methoxypyridin-3-yl)-4-morpholinothieno[3,2-d]pyrimidin-6-yl)methyl)(methyl)amino)pyrimidine-5-carboxamide Methanesulfonate (Methanesulfonate Salt of Compound 1)

Method A: To a mixture of Compound 1 (300 mg, 0.59 mmol) and MeOH/$Et_2O$ (3/1, 40 mL) was added a solution of methanesulfonic acid (114 mg, 1.18 mmol) in MeOH (3 mL) at 0° C. The resulting mixture was stirred at 0° C. for 3 h. The precipitate was collected by filtration and washed with $Et_2O$ to afford Compound 2 as a white solid (260 mg, 73%).

Method B: To a suspension of Compound 1 (1.5 g, 2.95 mmol) in dichloromethane/MeOH (40 mL/10 mL) was added methanesulfonic acid (341 mg, 3.55 mmol) in 2 mL MeOH at room temperature (15° C.) to form a clear solution. The reaction mixture was stirred at room temperature overnight. The reaction mixture was still clear. Ethyl acetate (40 mL) was added to the mixture and continued to stir for 3 h at room temperature. The resulting precipitate was collected by filtration to afford Compound 2 as a white solid (1.45 g, 83%).

m.p.: 179-185° C. LCMS: 509.3 [M+1]$^+$. $^1$H NMR (400 MHz, DMSO-$d_6$): δ 2.35 (s, 3H), 3.26 (s, 3H), 3.78 (t, J=9.6 Hz, 4H), 3.95 (s, 3H), 4.03 (t, J=9.2 Hz, 4H), 5.24 (s, 2H), 6.99 (d, J=8.8 Hz, 1H), 7.50 (s, 1H), 8.54 (dd, J=8.8 Hz, 2.4 Hz, 1H), 8.76 (s, 2H), 9.12 (d, J=2.4 Hz, 1H), 11.11 (br, 1H).

Example 3: Preparation of N-hydroxy-2-(((2-(6-methoxypyridin-3-yl)-4-morpholinothieno[3,2-d]pyrimidin-6-yl)methyl)(methyl)amino)pyrimidine-5-carboxamide Sodium Salt (Sodium Salt of Compound 1)

To a suspension of Compound 1 (300 mg, 0.59 mmol) in methanol (30 mL) at 0° C. was added slowly t-BuONa (85 mg, 0.88 mmol). The resulting mixture was warmed to room temperature and continued to stir for 2 h. The reaction was concentrated and the residue was triturated and washed with ethanol followed by filtration to afford Compound 3 as a white solid (230 mg, 73%). m.p.: 178-183° C. LCMS: 509.3 [M+1]$^+$. $^1$H NMR (400 MHz, DMSO-$d_6$): δ 3.17 (s, 3H), 3.75 (s, 4H), 3.92 (s, 7H), 5.16 (s, 2H), 6.90 (d, J=8.4 Hz, 1H), 7.42 (s, 1H), 8.57 (d, J=8.0 Hz, 1H), 8.65 (s, 2H), 9.14 (s, 1H).

Example 4: Preparation of N-hydroxy-2-(((2-(6-methoxypyridin-3-yl)-4-morpholinothieno[3,2-d]pyrimidin-6-yl)methyl)(methyl)amino)pyrimidine-5-carboxamide Potassium Salt (Potassium Salt of Compound 1)

To a mixture of Compound 1 (400 mg, 0.78 mmol) in methanol (50 mL) was added t-BuOK (132 mg, 1.17 mmol) at 0° C. under $N_2$. The mixture was stirred at 0° C. for 1 h and continued to stir at room temperature for 1.5 h. The insoluble solid was removed by filtration and the filtrate was cooled to −20° C. $Et_2O$ (100 mL) was added to the filtrate. The resulting mixture was stirred at −20° C. for 1 h. Hexanes (70 mL) was added and the mixture was continued to stir at −20° C. for 2 h. The solid was collected by filtration and dried in vacuo to afford Compound 4 as a white solid (150 mg, 35%). m.p.: 174-179° C. LCMS: 509.3[M+1]$^+$. $^1$H NMR (400 MHz, DMSO-$d_6$): δ 3.16 (s, 3H), 3.74-3.76 (m, 4H), 3.90-3.93 (m, 7H), 5.15 (s, 2H), 6.90 (d, J=8.4 Hz, 1H), 7.43 (s, 1H), 8.39 (br, 1H), 8.58 (d, J=8.8 Hz, 1H), 8.62 (s, 2H), 9.15 (s, 1H).

Example 5: Preparation of N-hydroxy-2-(((2-(6-methoxypyridin-3-yl)-4-morpholinothieno[3,2-d]pyrimidin-6-yl)methyl)(methyl)amino)pyrimidine-5-carboxamide Choline Salt (Choline Salt of Compound 1)

To a solution of Compound 1 (200 mg, 0.39 mmol) in DCM/MeOH (60 mL/12 mL) was added choline hydroxide (106 mg, 0.39 mmol, 45% in MeOH). The mixture was stirred at room temperature for 2 h and was then concentrated to remove ~30 mL of the solvent. Ethyl acetate (60 mL) was added and the mixture was stirred at room temperature for 2 h. After a small amount of precipitation occurred, the mixture was concentrated to remove ~40 mL of the solvent and additional ethyl acetate (60 mL) was added. The mixture was stirred at room temperature for 2 h and filtered to afford Compound 5 as a white solid (180 mg, 76%). m.p.: 181-185° C. LCMS: 509.3[M+1]$^+$. $^1$H NMR (400 MHz, DMSO-d$_6$): δ 3.11 (s, 9H), 3.17 (s, 3H), 3.40 (t, J=4.8 Hz, 2H), 3.75 (t, J=4.8 Hz, 4H), 3.84 (br, 2H), 3.90-3.93 (m, 7H), 5.15 (s, 2H), 6.89 (d, J=8.8 Hz, 1H), 7.41 (s, 1H), 8.57 (dd, J=8.8 Hz, 2.4 Hz, 1H), 8.64 (s, 2H), 9.14 (d, J=2.0 Hz, 1H).

Example 6: Preparation of N-hydroxy-2-(((2-(6-methoxypyridin-3-yl)-4-morpholinothieno[3,2-d]pyrimidin-6-yl)methyl)(methyl)amino)pyrimidine-5-carboxamide Sulfate (Sulfate Salt of Compound 1)

To a suspension of Compound 1 (200 mg, 0.39 mmol) in DCM/MeOH (30 mL/7.5 mL) was added sulfuric acid (77 mg, 0.79 mmol, in 1 mL MeOH) to form a clear solution. The reaction mixture was stirred at room temperature overnight. The precipitation occurred and tert-butyl methyl ether (60 mL) was then added. The resulting mixture was continued to stir for 1 h at room temperature. The solid was collected by filtration to afford Compound 6 as a white solid (180 mg, 76%). m.p.: 243-246° C. LCMS: 509.3 [M+1]$^+$. $^1$H NMR (400 MHz, DMSO-d$_6$): δ 3.26 (s, 3H), 3.78 (t, J=4.8 Hz, 4H), 3.96 (s, 3H), 4.03 (t, J=4.4 Hz, 4H), 5.24 (s, 3H), 6.98 (d, J=8.4 Hz, 1H), 7.50 (s, 1H), 8.54 (dd, J=8.8 Hz, 2.4 Hz, 1H), 8.76 (s, 2H), 9.12 (d, J=2.0 Hz, 1H), 11.06 (br, 1H).

Example 7: N-Hydroxy-2-(methyl((2-(6-(methylamino)pyridin-3-yl)-4-morpholinothieno[3,2-d]pyrimidin-6-yl)methyl)amino)pyrimidine-5-carboxamide (Compound 2)

Step 7a: (2-Chloro-4-morpholin-4-yl-thieno[3,2-d]pyrimidin-6-ylmethyl)-methyl-amine (Compound 0503)

To the solution of 0112 (20.0 g, 70.4 mmol) in methanol (125 mL) was added methylamine solution in methanol (27% v/v, 75 mL, 563.2 mmol) under nitrogen atmosphere. The reaction mixture was stirred at room temperature overnight and the solvent was removed in vacuo to give a crude solid product, which was dissolved in methanol (550 mL) and THF (220 mL) under nitrogen. Sodium borohydride (8 g, 211.2 mmol) was added in portions and reaction mixture was stirred at room temperature overnight. The reaction mixture was evaporated in vacuo and water (300 mL) was added. The aqueous mixture was extracted with methylene chloride and the combined extracts were dried over Na$_2$SO$_4$ and concentrated. The residue was dissolved in 6M HCl (230 mL) and stirred for 30 min. The aqueous solution was washed with methylene chloride for several times, and adjusted to pH=9-10 with NaOH (4N). The precipitated solid was collected by filtration and dried (60° C., 6 h) to give a light yellow solid (18 g, 85%).

LCMS: 299 [M+1]$^+$. $^1$H NMR (400 MHz, DMSO-d$_6$): δ 2.32 (s, 3H), 3.74 (t, J=5.2 Hz, 4H), 3.88 (t, J=5.2 Hz, 4H), 3.96 (s, 2H), 7.24 (s, 1H).

Step 7b: 2-[(2-Chloro-4-morpholin-4-yl-thieno[3,2-d]pyrimidin-6-ylmethyl)-methyl-amino]-pyrimidine-5-carboxylic Acid Ethyl Ester (Compound 0504)

The mixture of 0503 (10 g, 33.6 mmol), CH$_3$CN (400 mL) and 0305 (6.8 g, 36.4 mmol) was stirred at room temperature. Diisopropylethylamine (DIPEA) (220 mL, 1.26 mol) was then added and the solution was stirred overnight and evaporated. After methylene chloride (300 mL) was added, the organic phase was washed with water, dried over Na$_2$SO$_4$ and concentrated in vacuo to leave a residue. To the residue was added ethyl acetate and the mixture was stirred in ice/water bath for 50 min. The titled product 0504 was collected as a white solid (10.6 g, 70%). LCMS: 449 [M+1]$^+$; $^1$H NMR (400 MHz, DMSO-d$_6$): δ 1.30 (t, J=7.2 Hz, 3H), 3.25 (s, 3H), 3.71 (t, J=5.2 Hz, 4H), 3.83 (t, J=4.8 Hz, 4H), 4.29 (m, 2H), 5.21 (s, 2H), 7.39 (s, 1H), 8.87 (s, 2H).

Step 7c: Ethyl 2-(methyl((2-(6-(methylamino)pyridin-3-yl)-4-morpholinothieno[3,2-d]pyrimidin-6-yl)methyl)amino)pyrimidine-5-carboxylate (Compound 0603-111)

A mixture of N-methyl-5-(4,4,5,5-tetramethyl-1,3,2-dioxaborolan-2-yl)pyridin-2-amine (0602-227) (351 mg, 1.5 mmol), 0504 (314 mg, 0.7 mmol), NaHCO$_3$ (176 mg, 2.1 mmol) and Pd(PPh$_3$)$_2$Cl$_2$ (24.6 mg, 0.035 mmol) were dissolved in Toluene/EtOH/H$_2$O (2.5 mL/1.6 mL/0.7 mL). Then the reaction was stirred at 120° C. in microwave for 2 h. Water (8 mL) was added to the mixture and extracted with ethyl acetate (15 mL×3). The organic layer was dried, concentrated, purified by column chromatography (methanol in dichloromethane, 5% v/v) to give the title compound 0603-111 (150 mg, 41%) as a white solid. LCMS: 521 [M+1]$^+$. $^1$H NMR (400 MHz, DMSO-d$_6$): δ 1.28 (t, J=7.2 Hz, 3H), 2.81 (d, J=4.4 Hz, 3H), 3.24 (s, 3H), 3.73 (d, J=4.4 Hz, 4H), 3.86 (d, J=4.4 Hz, 4H), 4.27 (q, J=7.2 Hz, 2H), 5.20 (s, 2H), 6.48 (d, J=8.4 Hz, 1H), 6.91 (d, J=4.4 Hz, 1H), 7.39 (s, 1H), 8.25 (d, J=8.4 Hz, 1H), 8.86 (s, 2H), 8.90 (s, 1H).

Step 7d: N-Hydroxy-2-(methyl((2-(6-(methylamino)pyridin-3-yl)-4-morpholinothieno[3,2-d]pyrimidin-6-yl)methyl)amino)pyrimidine-5-carboxamide (Compound 2)

Compound 2 was prepared as a brown solid (21 mg, 14%) from 0603-236 (150 mg, 0.29 mmol) and a freshly prepared hydroxylamine methanol solution (6 mL) using a procedure similar to that described in Example 1: m.p. 193-195° C. LCMS: 508 [M+1]$^+$. $^1$H NMR (400 MHz, DMSO-d$_6$): δ 2.83 (d, J=4.8 Hz, 3H), 3.23 (s, 3H), 3.74 (m, 4H), 3.89 (m, 4H), 5.20 (s, 2H), 6.50 (d, J=8.8 Hz, 1H), 6.92 (d, J=5.2 Hz, 1H), 7.39 (s, 1H), 8.27 (dd, J=8.8, 2.0 Hz, 1H), 8.75 (s, 2H), 9.01 (d, J=2.0 Hz, 1H), 9.07 (br, 1H).

Example 8: 2-(((2-(4-aminophenyl)-4-morpholinothieno[3,2-d]pyrimidin-6-yl)methyl)(methyl)amino)-N-hydroxypyrimidine-5-carboxamide (Compound 3)

Step 8a: N-(4-bromophenyl)acetamide (Compound 0601-150)

To the solution of 4-bromoaniline (6.3 g, 63.7 mmol) in CH$_2$Cl$_2$ (50 mL) was added acetyl chloride (3.75 g, 47.7 mmol) and TEA (7.4 g, 73.4 mmol) at 0° C., stirred for 2 hours. The reaction mixture was washed with water, brine, dried over Na$_2$SO$_4$, filtered, and concentrated under reduced pressure to give the title compound 0601-150 (3.6 g, 46%) as a brown solid. LCMS: 214 [M+1]$^+$; $^1$H NMR (400 MHz, DMSO-d$_6$). δ 2.05 (s, 3H), 7.46 (d, J=8.8 Hz, 2H), 7.57 (d, J=8.8 Hz, 2H), 10.12 (s, 1H).

Step 8b: N-(4-(4,4,5,5-tetramethyl-1,3,2-dioxaborolan-2-yl)phenyl)acetamide (Compound 0602-150)

The title compound, 0602-150 was prepared (2.3 g, 94%) as a white solid from 0601-150 (2.0 g, 9.3 mmol), bis (pinacolato)diboron (4.4 g, 17.5 mmol), potassium acetate (3.5 g, 14 mmol), and PdCl$_2$(dppf)$_2$ (76 mg, 0.088 mmol) using a procedure similar to that described for compound 0602-107 (Example 34). LCMS: 262 [M+1]$^+$. $^1$H NMR (400 MHz, DMSO-d$_6$) δ 1.27 (d, J=6.8 Hz, 12H), 2.04 (s, 3H), 7.58 (s, 4H), 10.03 (s, 1H).

Step 8c: Ethyl 2-(((2-(4-aminophenyl)-4-morpholinothieno[3,2-d]pyrimidin-6-yl)methyl)(methyl) amino)pyrimidine-5-carboxylate (Compound 0603-150)

A mixture of compound 0504-54 (210 mg, 0.46 mmol), 0602-150 (159 mg, 0.60 mmol), sodium hydrogen carbonate (118 mg, 1.4 mmol), and bis(triphenylphosphine)palladium (II) chloride (17 mg, 0.02 mmol) in toluene (4 mL), ethanol (2 mL) and water (1 mL) was flushed with nitrogen and heated under microwave irradiation at 120° C. for 2 h. The reaction mixture was partitioned between ethyl acetate and water, organic layer was washed with brine, dried over magnesium sulfate, filtered and evaporated in vacuum. The residue was washed with dichloromethane to obtain ethyl 2-(((2-(4-acetamidophenyl)-4-morpholinothieno-[3,2-d]pyrimidin-6-yl)methyl)(methyl)amino)pyrimidine-5-carboxylate (136 mg, 53%) as a white solid. LCMS: 548 [M+1]$^+$, $^1$H NMR (400 MHz, DMSO-d$_6$): δ 1.29 (t, J=7.2 Hz, 3H), 2.06 (s, 6H), 3.26 (s, 3H), 3.75 (m, 4H), 3.91 (m, 4H), 4.28 (q, J=7.2 Hz, 2H), 5.22 (s, 2H), 7.45 (s, 1H), 7.67 (d, J=8.8 Hz, 1H), 8.31 (d, J=8.8 Hz, 1H), 8.87 (s, 1H), 10.10 (s, 1H).

To the solution of above ethyl ester (280 mg, 0.51 mmol) in THF (10 mL) was added aqueous HCl solution (6M, 15 mL) at 40° C., stirred for 2 hours, the reaction mixture was neutralized with NaHCO$_3$ and extracted with CH$_2$Cl$_2$, the organic layer was washed with water, brine, dried over Na$_2$SO$_4$, filtered, and concentrated, purified by column chromatography (methanol in dichloromethane, 2% v/v), to give title compound 0603-150 (180 mg, 48%) as a white solid. LCMS: 506 [M+1]$^+$. $^1$H NMR (400 MHz, DMSO-d$_6$) δ 1.29 (t, J=7.6 Hz, 3H), 3.24 (s, 3H), 3.73 (m, 4H), 3.86 (m, 4H), 4.27 (q, J=6.8 Hz, 2H), 5.20 (s, 2H), 6.59 (d, J=8.8 Hz, 2H), 7.36 (s, 1H), 8.07 (d, J=8.0 Hz, 2H), 8.86 (s, 1H).

Step 8d: 2-(((2-(4-aminophenyl)-4-morpholinothieno[3,2-d]pyrimidin-6-yl)methyl)(methyl)amino)-N-hydroxypyrimidine-5-carboxamide (Compound 3)

Compound 3 was prepared (43 mg, 26%) as a yellow solid from 0603-150 (170 mg, 0.3 mmol) and freshly prepared hydroxylamine methanol solution (4 mL) using a procedure similar to that described in Example 1. m.p. 183-186° C. LCMS: 493 [M+1]$^+$; $^1$H NMR (400 MHz, DMSO-d$_6$): δ 3.22 (s, 3H), 3.74 (m, 4H), 3.87 (m, 4H), 4.27 (q, J=6.8 Hz, 2H), 5.20 (s, 2H), 5.50 (s, 2H), 6.59 (d, J=8.8 Hz, 2H), 7.36 (s, 1H), 8.07 (d, J=8.0 Hz, 2H), 8.86 (s, 2H).

Example 9: PI3 Kinase Activity Assay

The following assays were used to determine the ability of Compound 1 to inhibit various isoforms and mutants of PI3K.

PI3Kα

PI3Kα activity was measured using ADP-Glo luminescent kinase assay. PI3Kα, a complex of N-terminal GST-tagged recombinant full-length human p110α and untagged recombinant full length human p85α were coexpressed in a Baculovirus infected Sf9 cell expression system. (GenBank Accession No. for p110α, U79143; for p85α, XM_043865). The proteins were purified by one-step affinity chromatography using glutathione-agarose. A competition assay was performed to measure the amount of ADP generated from ATP in the presence of purified recombinant PI3Kα (p110α/p85α) and PIP2. PI3Kα was incubated with 20 μM PIP2 substrate in the reaction buffer (50 mM HEPES, pH 7.4, 150 mM NaCl, 5 mM MgCl2, 3 μM Na orthovanadate, 1 mM DTT, 10 μM ultrapure ATP and 0.5% DMSO) for 30 minutes at 30° C. The ADP generated in the reaction was then measured by the ADP-Glo Assay. The assay was performed in two steps; first an equal volume of ADP-GLO™ Reagent (Promega) was added to terminate the kinase reaction and deplete the remaining ATP. In the second step, the Kinase Detection Reagent was added, which simultaneously converts ADP to ATP. The newly synthesized ATP was measured using coupled luciferase/luciferin reaction. The IC$_{50}$ determined for Compound 1 in this assay was less than 100 nM.

The ability of Compound 1 to inhibit the PI3Kα mutants H1047R and E545K was also determined using the general procedure described above. The IC$_{50}$ determined for both mutants was less than 100 nm.

PI3Kβ

Activity of PI3Kβ was measured using time-resolved fluorescence resonance energy transfer (TR-FRET) assay utilizing homogenous time resolved fluorescence (HTRF) technology. PI3Kβ, a complex of N-terminal histidine-tagged recombinant full-length human p110β and untagged recombinant full length human p85α were coexpressed in a Baculovirus infected Sf21 cell expression system. (GenBank Accession No. for p110β, NM_006219; for p85α, XM_043865). The proteins are purified by one-step affinity chromatography using glutathione-agarose. A competition assay was performed to measure the amount of PIP3 generated from PIP2 in the presence of purified recombinant PI3Kbeta (p110β/p85α). PI3Kβ was incubated with 10 μM PIP2 substrate in the reaction buffer (20 mM HEPES, pH 7.5, 10 mM NaCl, 4 mM MgCl$_2$, 2 mM DTT, 10 μM ATP and 1% DMSO) for 30 minutes at 30° C. The reaction product was then mixed with a PIP3 detector protein, europium-labeled antibody, biotin-labeled PIP3 probe and allophycocyanin-labeled Streptavidin. A sensor complex is formed to generate a stable TR-FRET signal in the reaction mixture. This signal intensity decrease as biotin-labeled probe binding to the PIP3 detector is displaced by PIP3 produced by enzymatic activity and the amount of unbound biotin-labeled PIP3 probe in the mixture increases. TR-FRET signal was determined using microplate reader with background subtraction.

The IC$_{50}$ determined for Compound 1 in this assay was between 100 and 1000 nM.

PI3Kδ

Activity of PI3Kδ was measured using fluorescence polarization assay. PI3Kδ, a complex of N-terminal histidine-tagged recombinant full-length human p110δ and untagged recombinant full length human p85α were coexpressed in a Baculovirus infected Sf9 cell expression system. (GenBank Accession No. for p110δ, NM_005026). The proteins are purified by one-step affinity chromatography using glutathione-agarose. A competition assay was performed to measure the amount of PIP3 generated from PIP2 in the presence of purified recombinant PI3Kδ (p110δ/p85α). PI3Kδ was incubated with 10 µM PIP2 substrate in the reaction buffer (20 mM HEPES (pH 7.5), 10 mM NaCl, 4 mM MgCl$_2$, 2 mM DTT, 10 µM ATP and 1% DMSO) for 1 hour at 30° C. The reaction product was then mixed with a PIP3 detector protein and the fluorescent PIP3 probe. Polarization (mP) values decrease as fluorescent probe binding to the PIP3 detector is displaced by PIP3 produced by enzymatic activity and the amount of unbound fluorescent probe in the mixture increases. Polarization degrees (mP) value was determined using microplate reader with background subtraction.

The IC$_{50}$ determined for Compound 1 in this assay was less than 100 nM.

PI3Kγ

Activity of PI3Kγ was measured using time-resolved fluorescence resonance energy transfer (TR-FRET) assay utilizing homogenous time resolved fluorescence (HTRF) technology. N-terminal histidine tagged human PI3Kδ was expressed in a Baculovirus infected Sf9 cell expression system. (GenBank Accession AF327656). The proteins are purified by one-step affinity chromatography using glutathione-agarose. A competition assay was performed to measure the amount of PIP3 generated from PIP2 in the presence of purified recombinant PI3Kγ (p120γ). PI3Kγ (2 nM) was incubated with 10 µM PIP2 substrate in the reaction buffer (20 mM HEPES, pH 7.5, 10 mM NaCl, 4 mM MgCl$_2$, 2 mM DTT, 10 µM ATP and 1% DMSO) for 30 minutes at 30° C. The reaction product was then mixed with a PIP3 detector protein, europium-labeled antibody, biotin-labeled PIP3 probe and allophycocyanin-labeled Streptavidin. A sensor complex is formed to generate a stable TR-FRET signal in the reaction mixture. This signal intensity decrease as biotin-labeled probe binding to the PIP3 detector is displaced by PIP3 produced by enzymatic activity and the amount of unbound biotin-labeled PIP3 probe in the mixture increases. TR-FRET signal was determined using microplate reader with background subtraction.

The IC$_{50}$ determined for Compound 1 in this assay was between 100 and 1000 nM.

Example 10: HDAC Activity Assay

HDAC inhibitory activity was assessed using the Biomol Color de Lys system (AK-500, Biomol, Plymouth Meeting, PA). Briefly, HeLa cell nuclear extracts were used as a source of HDACs. Different concentrations of test compounds were serially diluted in dimethylsulfoxide (DMSO) and added to HeLa cell nuclear extracts in the presence of a colorimetric artificial substrate. Final assay condition contained 50 mM Tris/C$_1$, pH 8.0, 137 mM NaCl, 2.7 mM KCl and 1 mM MgCl$_2$. Reactions were carried in room temperature (25° C.) for 1 hour before addition of developer for termination. Relative enzyme activity was measured in the WALLAC Victor II 1420 microplate reader as fluorescence intensity (excitation: 350-380 nm; emission: 440-460 nm). Data were analyzed using GraphPad Prism (v4.0a) with a sigmoidal dose response curve fitting for IC$_{50}$ calculation. The IC$_{50}$ determined for Compound 1 in this assay was less than 100 nM.

The activities of Compound 1 against HDAC isotypes were also determined. HDAC specificity assays were performed at BPS Bioscience (San Diego, CA), following their standard operating procedure. Briefly, purified flag- (human HDAC-1), NCOR2- (human HDAC3), GST- (human HDAC4, 6, 7, 10 and 11) or His- (human HDAC 2, 5, 8 and 9) tagged enzymes were expressed in 519 insect cells and purified before use. The substrate used for HDAC1, 2, 3, 6, 7, 8, 9 and 11 was HDAC Substrate 3 developed by BPS Bioscience. For other HDAC enzymes, HDAC Class 2a substrate was used. All enzymatic reactions were conducted in duplicate at 37° C. for 30 minutes, except HDAC11 enzyme assay, which was conducted at room temperature for 3 hours.

The table below sets forth the results for each of HDACs 1-11, with IC$_{50}$ values provided as follows: I>1000 nM; 100 nM<II<1000 nM; 10 nM<III<100 nM; IV<10 nM.

| | HDAC | | | | | | | | | |
|---|---|---|---|---|---|---|---|---|---|---|
| | 1 | 2 | 3 | 8 | 4 | 5 | 6 | 7 | 9 | 10 | 11 |
| IC$_{50}$ | IV | IV | IV | II | II | II | III | II | II | IV | IV |

Example 11: Study of Compound 1 and Anti-PD-1 in the Mouse Xenograft Model-CTW26.WT Mouse Colon Carcinoma Cells Animals: Female Balb/c Mice, 8 weeks old, fed a high fat diet Compounds:
  Compound 1: dosed PO at 50 mg/kg at a 5 days on, 2 days off schedule (5+2−)
  Isotype Control: LEAF™ Purified Rat IgG2a, obtained from BioLegend™, San Diego, CA; dosed IP at 100 ug/mouse, BIW.
  PD-1 antibody: LEAF™ rat anti-mouse CD279 (PD-1), clone 29F.1A12, obtained from BioLegend™, San Diego, CA; dosed IP at 100 ug/mouse, BIW.

Administration of Cells:
  CT26.WT cells were collected from flasks and washed once in RPMI 1640 with no additives. Final concentrations were reached in plain media (RPMI-1640) and kept on ice until administration to mice. Mice were grouped once tumors were palpable on day 7 or day 8 and randomized by body weight. Treatment started with antibody and Compound 1 was begun immediately.

Grouping:

| Group | N | Dosing Details |
|---|---|---|
| 1 | 8 | Vehicle (Compound 1 vehicle—30% CAPTISOL ™) |
| 2 | 8 | Compound 1 50 mg/kg (5 + 2-) |
| 3 | 8 | Negative Isotype 100 ug/mouse (QD 2 × week) |
| 4 | 8 | Anti-PD-1 (1A12) 100 ug/mouse (QD 2 × week) |
| 5 | 8 | Compound 1 50 mg/kg (5 + 2-) Negative Isotype 100 ug/mouse (QD 2 × week) |
| 6 | 8 | Compound 1 50 mg/kg (5 + 2-) Anti-PD-1 (1A12) 100 ug/mouse (QD 2 × week) |

Study Schedule:
  Animals were monitored until the dosing commenced and then were measured twice a week during dosing until tumor volume reached protocol limit or ulceration was too severe. Tumor tissue and blood/plasma were collected at the end of the study.

Results

The results of this study are presented in the table below and in FIG. 1. Groups 1-3 had 7 mice that were evaluable. In Groups 4-6, all 8 mice were evaluable. Compound 1 alone at 50 mg/kg showed only small inhibition of tumor growth. Anti-PD-1 showed greater tumor growth inhibition, but still under 50%. The combination of Compound 1 and anti-PD-1, however, showed almost complete inhibition of tumor growth.

| Drug | Dosage | TGI %* (Day 15) | P value* (T-test) | #mice (Day 15) |
|---|---|---|---|---|
| Vehicle (Cpd 1) | — | na | na | 7/8 |
| Isotype mAb control | 100 µg | na | na | 7/8 |
| Cpd 1 | 50 mg/kg | 3 | ns | 7/8 |
| Cpd 1 + isotype mAb | 50 mg/kg + 100 µg | 16 | ns | 8/8 |
| anti-PD-1 mAb | 100 µg | 44 | <0.05 | 8/8 |
| Cpd 1 + anti-PD-1 mAb | 50 mg/kg + 100 µg | 97 | <0.0001 | 8/8 |

*Relative to Vehicle (Cmp 1) group

Example 12: Study of Compound 1 and Anti-PD-1 in the A20 Mouse Xenograft Model

Animals: Female Balb/c Mice, 4-5 weeks old, fed a regular diet
Compounds:
  Compound 1: dosed PO at 50 mg/kg or 100 mg/kg at a 5 days on, 2 days off schedule (5+2−).
  Isotype Control: LEAF™ Purified Rat IgG2a, obtained from BioLegend™, San Diego, CA; dosed IP at 100 ug/mouse, BIW, 3 weeks.
  Anti-PD-1 antibody: LEAF™ rat anti-mouse CD279 (PD-1), clone 29F.1A12, obtained from BioLegend™, San Diego, CA; dosed at 100 ug/mouse, BIW, 3 weeks.
  Vehicle: Compound 1 vehicle-30% Captisol™; dosed 5+2−, PO, 3 weeks.
Administration of Cells:
  A20 syngeneic cells were collected from flasks and washed once in RPMI 1640 with no additives. Final concentrations were reached in plain media (RPMI-1640) and kept on ice until administration to mice. Animals were implanted with 2×10$^5$ cells in the right flank. Dosing commenced when tumors were greater than 100 mm$^3$ (around day 13) and dosing continued for 21 days or until the tumors reached the limit of 2000 mm$^3$.
Grouping:

| Group | N | Dosing Details |
|---|---|---|
| 1 | 8 | Vehicle Isotype control |
| 2 | 8 | Anti-PD-1 |
| 3 | 8 | Compound 1, 100 mg/kg |
| 4 | 8 | Compound 1, 100 mg/kg Anti-PD-1 |

Figure 2:
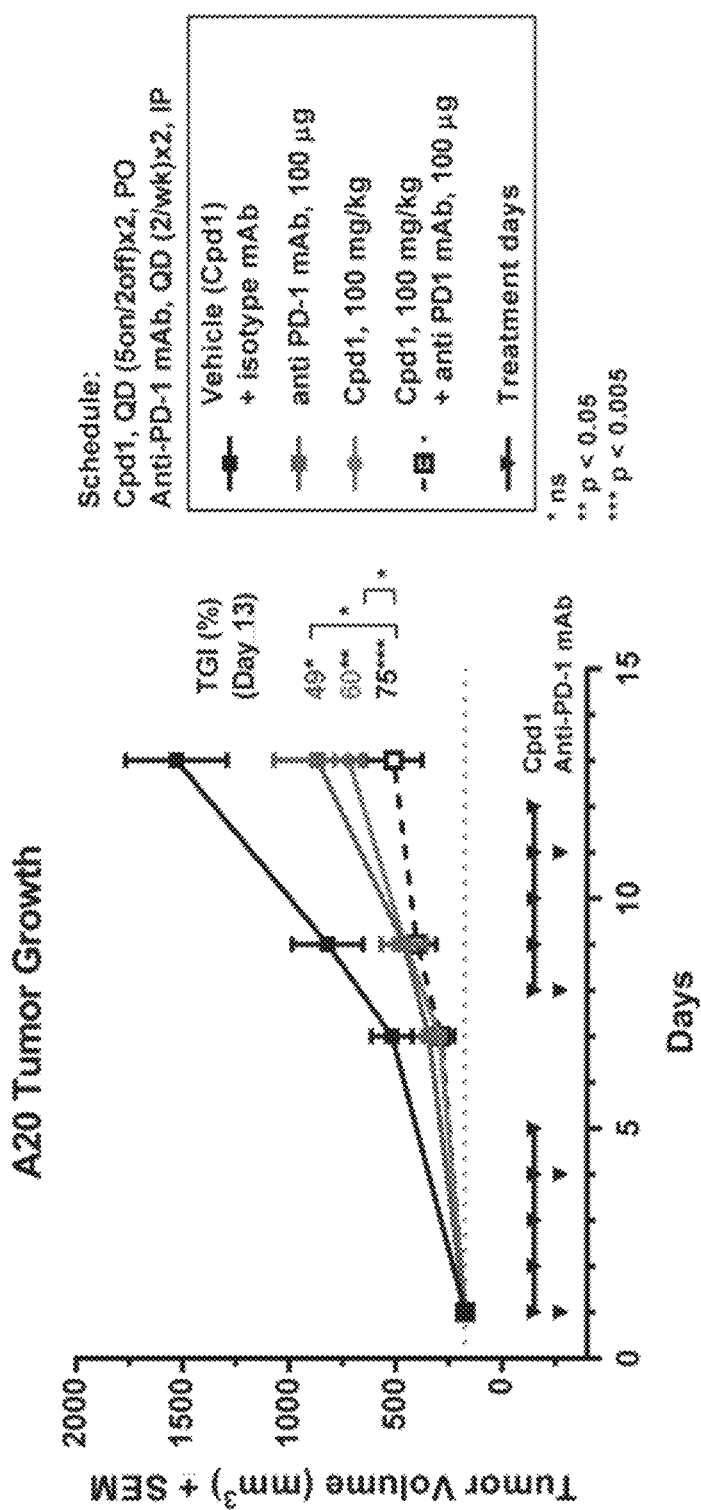
FIG. 2 is a graph of tumor volume versus time in the mouse A20 xenograft model as described in Example 12.

Study Schedule:
  Animals started dosing around day 13 when tumors are fully palpable and measured. Dosing continued until tumors begin to show ulceration that requires sacrifice. Tumors were collected before extensive necrosis to run ELISA and Flow analysis.
Results
  The results of this study are presented in the Table below and in FIG. 2. Both Compound 1 alone at 100 mg/kg and anti-PD-1 alone showed significant tumor growth inhibition. The combination of Compound 1 and anti-PD-1 showed greater tumor growth inhibition than either agent alone.

| Drug | Dosage | TGI %* (Day 13) | P value* (T-test) | #mice (Day 13) |
|---|---|---|---|---|
| Vehicle (Cpd 1) + isotype | — | na | na | 8/8 |
| anti-PD-1 mAb | 100 µg | 49 | ns | 8/8 |
| Cpd 1 | 100 mg/kg | 60 | <0.05 | 8/8 |
| Cpd 1 + anti-PD-1 mAb | 100 mg/kg + 100 µg | 75 | <0.005 | 8/8 |

*Relative to Vehicle (Cmp 1) + isotype group

The patent and scientific literature referred to herein establishes the knowledge that is available to those with skill in the art. All United States patents and published or unpublished United States patent applications cited herein are incorporated by reference. All published foreign patents and patent applications cited herein are hereby incorporated by reference. All other published references, documents, manuscripts and scientific literature cited herein are hereby incorporated by reference.

While this invention has been particularly shown and described with references to preferred embodiments thereof, it will be understood by those skilled in the art that various changes in form and details may be made therein without departing from the scope of the invention encompassed by the appended claims.

What is claimed is:
1. A method of treating colon carcinoma in a subject in need thereof, comprising administering to the subject:
  (a) a pharmaceutically acceptable salt of a compound of the formula:

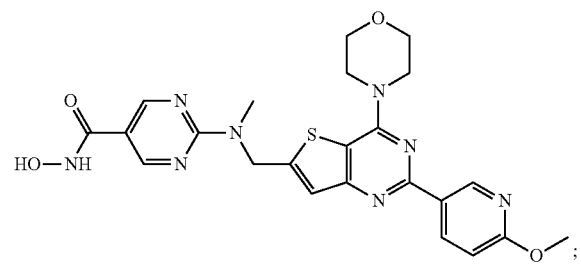 [SMILES: COc1ccc(-c2nc(N3CCOCC3)c3sc(CN(C)c4ncc(C(=O)NO)cn4)cc3n2)cn1]

and
  (b) a PD-1 signaling inhibitor, wherein the pharmaceutically acceptable salt of the compound and the PD-1 signaling inhibitor are administered in amounts which in combination are therapeutically effective.
2. The method of claim 1, wherein the PD-1 signaling inhibitor is an inhibitor of one or more of PD-1, PD-L1, and PD-L2.
3. The method of claim 2, wherein the PD-1 signaling inhibitor inhibits PD-1 or PD-L1.
4. The method of claim 2 wherein the PD-1 signaling inhibitor is an anti-PD-1 monoclonal antibody, an anti-PD-L1 monoclonal antibody or an anti-PD-L2 monoclonal antibody.
5. The method of claim 2, wherein the PD-1 signaling inhibitor is pembrolizumab, nivolumab, atelolizumab, avelumab, durvalumab or pidilizumab.
6. The method of claim 5, wherein the PD-1 signaling inhibitor is pembrolizumab or nivolumab.

7. The method of claim 1, wherein the pharmaceutically acceptable salt of the compound and the PD-1 signaling inhibitor are administered in a single composition.

8. The method of claim 1, wherein the pharmaceutically acceptable salt is administered orally in the form of a tablet or capsule.

9. The method of claim 1 wherein the pharmaceutically acceptable salt is a methanesulfonate salt or a benzenesulfonate salt.

* * * * *